United States Patent
Slavcev et al.

(10) Patent No.: US 10,736,955 B2
(45) Date of Patent: Aug. 11, 2020

(54) FUSION PROTEIN COMPRISING BACTERIOPHAGE λ GPD FUSED TO A GP2 ANTIGEN DERIVED FROM HER-2/NEU

(71) Applicant: Theraphage Inc., Kitchener (CA)

(72) Inventors: Roderick A. Slavcev, Kitchener (CA); Javad Behravan, Thornhill (CA)

(73) Assignee: Theraphage Inc., Kitchener (CA)

( * ) Notice: Subject to any disclaimer, the term of this patent is extended or adjusted under 35 U.S.C. 154(b) by 0 days.

(21) Appl. No.: 16/562,132

(22) Filed: Sep. 5, 2019

(65) Prior Publication Data

US 2020/0030433 A1  Jan. 30, 2020

Related U.S. Application Data

(63) Continuation of application No. PCT/IB2018/001428, filed on Nov. 21, 2018.

(60) Provisional application No. 62/590,326, filed on Nov. 23, 2017.

(51) Int. Cl.
| | |
|---|---|
| *A61P 35/00* | (2006.01) |
| *A61K 39/00* | (2006.01) |
| *C07K 14/005* | (2006.01) |
| *C07K 14/47* | (2006.01) |
| *C07K 14/82* | (2006.01) |
| *A61K 39/12* | (2006.01) |
| *C12N 7/00* | (2006.01) |

(52) U.S. Cl.
CPC ...... *A61K 39/12* (2013.01); *A61K 39/001106* (2018.08); *A61P 35/00* (2018.01); *C07K 14/005* (2013.01); *C07K 14/4748* (2013.01); *C07K 14/82* (2013.01); *C12N 7/00* (2013.01); *A61K 2039/585* (2013.01); *C07K 2319/40* (2013.01); *C12N 2795/10322* (2013.01); *C12N 2795/10334* (2013.01); *C12N 2795/10371* (2013.01)

(58) Field of Classification Search
None
See application file for complete search history.

(56) References Cited

U.S. PATENT DOCUMENTS

| 7,981,632 B2 | 7/2011 | Schmidt |
| 2007/0020232 A1 | 1/2007 | Rossignol et al. |

FOREIGN PATENT DOCUMENTS

| WO | WO-9504069 A1 | 2/1995 |
| WO | WO-2004076670 A1 | 9/2004 |
| WO | WO-2017149150 A1 | 9/2017 |
| WO | WO-2017185169 A1 | 11/2017 |
| WO | WO-2019102265 A1 | 5/2019 |

OTHER PUBLICATIONS

Altschul et al.: Basic Local Alignment Search Tool. J. Mol. Biol. 215: 403-410 (1990).
Andreasson et al.: Murine pneumotropic virus chimeric Her2/neu virus-like particles as prophylactic and therapeutic vaccines against Her2/neu expressing tumors. International journal of cancer, 124(1): 150-156 (2009).
Arab et al., Lambda phage nanoparticles displaying HER2-derived E75 peptide induce effective E75-CD8+ T response. Immunologic Research 66(1):200-206 (2018).
Arnon et al.: Complexes and Conjugates of CIS-Pt for Immunotargeted Chemotherapy. Adv. Ex Med. Biol. 303, 79-90 (1991).
Barati et al.: Nanoliposomes carrying HER2/neu-derived peptide AE36 with CpG-ODN exhibit therapeutic and prophylactic activities in a mice TUBO model of breast cancer. Immunology Letters (2017).
Baxevanis et al., Immunogenic HER-2/neu peptides as tumor vaccines. Cancer Immunology Immunotherapy 55(1):85-95 (2006).
Beghetto et al.: Lambda-display: a powerful tool for antigen discovery. Molecules; 16(4): 3089-3105 (2011).
Bona, C.A., S. Casares, and T.-D. Brumeanu, Towards development of T-cell vaccines. Immunology today, 19(3): 126-133 (1998).
Bot et al.: Kinetics of generation and persistence on membrane class II molecules of a viral peptide expressed on foreign and self proteins. The Journal of Immunology, 157(8): 3436-3442 (1996).
Brossart et al.: Induction of cytotoxic T-lymphocyte responses in vivo after vaccinations with peptide pulsed dendritic cells. Blood; 96(9): 3102-3108 (2000).
Brunner et al.: Quantitative assay of the lytic action of immune lymphoid cells of 51Cr-labelled allogeneic target cells in vitro; inhibition by isoantibody and by drugs. Immunology, 14(2): 181 (1968).
Carmichael et al.: Results of the first phase 1 clinical trial of the HER-2/neu peptide (GP2) vaccine in disease-free breast cancer patients. Cancer, 116(2): 292-301 (2010).
Chikh et al.: Efficient delivery of Antennapedia homeodomain fused to CTL epitope with liposomes into dendritic cells results in the activation of CD8+ T cells. The Journal of Immunology, 167(11): 6462-6470 (2001).
Clark et al.: Bacterial viruses as human vaccines? Expert review of vaccines, 3(4): 463-476 (2004).
Clark et al.: March, Bacteriophages and biotechnology: vaccines, gene therapy and antibacterials. Trends in biotechnology, 24(5): 212-218 (2006).
De La Cruz et al.: Immunogenicity and epitope mapping of foreign sequences via genetically engineered filamentous phase. Journal of Biological Chemistry; 263(9): 4318-4322 (1988).
De Temmerman et al.: Particulate vaccines: on the quest for optimal delivery and immune response. Drug discovery today, 16(13): 569-582 (2011).
DeBerardinis et al.: Phage display of peptide epitopes from HIV-1 elicits strong cytolytic response. Nature biotechnology; 18(8): 873-876 (2000).

(Continued)

*Primary Examiner* — Nicole Kinsey White
(74) *Attorney, Agent, or Firm* — Wilson Sonsini Goodrich & Rosati

(57) ABSTRACT

Described herein is a fusion protein comprising a bacteriophage protein fused to a cancer antigen. Vaccines are also described, as well as methods of treatment and/or prevention of cancer and methods of immunizing an individual.

17 Claims, 7 Drawing Sheets

Specification includes a Sequence Listing.

(56) References Cited

OTHER PUBLICATIONS

Disis et al.: Pre-existent immunity to the HER-2/neu oncogenic protein in patients with HER-2/new overexpressing breast and ovarian cancer. Breast cancer research and treatment, 62(3): 245-252 (2000).
Doucette-Stamm et al., Nucleic acid sequences and expression system relating to Enterococcus faecium for diagnostics and therapeutics. Sequence 5309 from patent U.S. Pat. No. 6583275, GenBank Accession No. AAQ44751 dated Aug. 17, 2016. Retrieved from https://www.ncbi.nlm.nih.gov/protein/aaq44751.
Eguchi et al.: Protein transduction domain of HIV-1 Tat protein promotes efficient delivery of DNA into mammalian cells. Journal of Biological Chemistry, 276(28): 26204-26210 (2001).
Fixen et al., Phosphoribosyl-ATP pyrophosphatase [*Methyloversatilis* sp. RAC08]. GenBank Accession No. AOF80385 dated Aug. 25, 2016. Retrieved from https://www.ncbi.nlm.nih.gov/protein/AOF80385.
Fixen et al., S4 domain protein [*Methyloversatilis* sp. RAC08]. GenBank Accession No. AOF80381.1 dated Aug. 225, 2016. Retrieved from https://www.ncbi.nlm.nih.gov/protein/AOF80381.
Fixen et al., Short chain dehydrogenase family protein [*Methyloversatilis* sp. RAC08]. GenBank Accession No. AOF80392 dated Aug. 25, 2016. Retrieved from https://www.ncbi.nlm.nih.gov/protein/AOF80392.
Gao et al.: Phage display and its application in vaccine design. Annals of microbiology; 60(1): 13-19 (2010).
Greenfield et al.: Evaluation in Vitro of Adriamycin Immunoconjugates Synthesized Using an Acid-sensitive Hydrazone Linker. Cancer Research 50, 6600-6607 (1990).
Gupta et al.: High-density functional display of proteins on bacteriophage lambda. Journal of molecular biology, 334(2): 241-254 (2003).
Gutschalk et al.: GM-CSF enhances tumor invasion by elevated MMP-2,-9, and-26 expression. Cancer medicine, 2(2): 117-129 (2013).
Hashemi et al.: Evaluation of humoral and cellular immune responses against HSV-1 using genetic immunization by filamentous phage particles: a comparative approach to conventional DNA vaccine. Journal of virological methods, 163(2): 440-444 (2010).
Hashemi et al.: Immunization with M2e-displaying T7 bacteriophage nanoparticles protects against influenza A virus challenge. PloS ONE; 7(9): e45765 (2012).
Hayes et al.: Dual expression system for assembling phage lambda display particle (LDP) vaccine to porcine Circovirus 2 (PCV2). Vaccine; 28(41): 6789-6799 (2010).
Huang et al.: Disterolphospholipids: nonexchangeable lipids and their application to liposomal drug delivery. Angewandte Chemie International Edition, 48(23): 4146-4149 (2009).
Kalnioa et al.: Evaluation of T7 and lambda phage display systems for survey of autoantibody profiles in cancer patients. Journal of immunological methods, 334(1): 37-50 (2008).
Karlin et al.: Methods for assessing the statistical significance of molecular sequence features by using general scoring schemes. Proc. Natl. Acad. Sci. 87: 2264-2268 (1990).
Kiseleva et al.: Mol. Biol. (USSR)25, 508-514 (1991).
Kopf et al.: IL-4-deficient Balb/c mice resist infection with Leishmania major. Journal of Experimental Medicine, 184(3): 1127-1136 (1996).
Layton et al.: Induction of single and dual cytotoxic T-lymphocyte responses to viral proteins in mice using recombinant hybrid Ty-virus-like particles. Immunology, 87(2): 171-178 (1996).
Lichtenfels et al.: CARE-LASS (calcein-release-assay), an improved fluorescence-based test system to measure cytotoxic T lymphocyte activity. Journal of immunological methods, 172(2): 227-239 (1994).
Liolios et al., Complete genome sequence of Thermobispora bispora type strain (R51). Glycoside hydrolase family 65 central catalytic [Thermobispora bispora DSM 43833]. GenBank Accession No. ADG89586 dated Dec. 11, 2013. Retrieved from https://www.ncbi.nlm.nih.gov/protein/adg89586.

Malik et al.: Role of capsid structure and membrane protein processing in determining the size and copy number of peptides displayed on the major coat protein of filamentous bacteriophage. Journal of molecular biology; 260(1): 9-21 (1996).
Mikawa et al.: Surface display of proteins on bacteriophage a heads. Journal of molecular biology, 262(1): 21-30 (1996).
Minenkova et al.: Identification of tumor-associated antigens by screening phage-displayed human cDNA libraries with sera from tumor patients. International journal of cancer, 106(4): 534-544 (2003).
Mittendorf et al.: Evaluation of the CD107 cytotoxicity assay for the detection of cytolytic CD8+ cells recognizing HER2/neu vaccine peptides. Breast cancer research and treatment; 92(1): 85-93 (2005).
Mittendorf et al.: Evaluation of the HER2/neu-derived peptide GP2 for use in a peptide-based breast cancer vaccine trial. Cancer, 106(11): 2309-2317 (2006).
Nilsson et al.: The use of phage display for the development of tumour targeting agents. Advanced drug delivery reviews, 43(2): 165-196 (2000).
Parmiani et al.: Universal and stemness-related tumor antigens: potential use in cancer immunotherapy. Clinical Cancer Research, 13(19): 5675-5679 (2007).
PCT/IB2018/001428 International Search Report and Written Opinion dated Mar. 21, 2019.
Prisco et al.: Filamentous bacteriophage fd as an antigen delivery system in vaccination. International journal of molecular sciences, 13(4): 5179-5194 (2012).
Purcell et al.: More than one reason to rethink the use of peptides in vaccine design. Nature reviews Drug discovery; 6(5): 404-414 (2007).
Rochman, Sue: New peptide vaccine for HER2-expressing breast tumors. Journal of the National Cancer Institute; 107(2): djv022 (2015).
Sartorius et al.: The use of filamentous bacteriophage fd to deliver MAGE-A10 or MAGE-A3 HLA-A2 restricted peptides and to induce strong antitumor CTL responses. The Journal of Immunology; 180(6): 3719-3728 (2008).
Schneble et al. Primary analysis of the prospective, randomized, phase II trial of GP2+ GM-CSF vaccine versus GM-CSF alone administered in the adjuvant setting to high-risk breast cancer patients. In ASCO Annual Meeting Proceedings. (2014).
Sokolenko et al.: Graphical analysis of flow cytometer data for characterizing controlled fluorescent protein display on λ phage. Cytometry Part A, 81(12): 1031-1039 (2012).
Souza et al.: Recombinant viruses as vaccines against viral diseases. Brazilian Journal of Medical and Biological Research; 38(4): 509-522 (2005).
Spergel et al.: Epicutaneous sensitization with protein antigen induces localized allergic dermatitis and hyperresponsiveness to methacholine after single exposure to aerosolized antigen in mice. Journal of Clinical Investigation, 101(8): 1614 (1998).
Spurrell et al.: Adaptive immunity in cancer immunology and therapeutics. Ecancermedicalscience; 8: 10 pages (2014).
Sternberg, et al.: Display of peptides and proteins on the surface of bacteriophage lambda. Proceedings of the National Academy of Sciences, 92(5): 1609-1613 (1995).
Thomas et al.: Peptide vaccination is superior to genetic vaccination using a recombineered bacteriophage λ subunit vaccine. Vaccine, 30(6): 998-1008 (2012).
Ulivieri et al.: Antigenic properties of HCMV peptides displayed by filamentous bacteriophages vs. synthetic peptides. Immunology letters; 119(1): 62-70 (2008).
Yang et al.: Novel fold and capsid-binding properties of the λ-phage display platform protein gpD. Nature Structural & Molecular Biology, 7(3): 230-237 (2000).
Yang et al.: Prophylactic vaccination with phage-displayed epitope of C. albicans elicits protective immune responses against systemic candidiasis in C57BL/6 mice. Vaccine, 23(31): 4088-4096 (2005).
Zucconi et al.: Selection of ligands by panning of domain libraries displayed on phage lambda reveals new potential partners of synaptojanin 1. Journal of molecular biology, 307(5): 1329-1339 (2001).

FUSION PROTEIN COMPRISING BACTERIOPHAGE λ GPD FUSED TO A GP2 ANTIGEN DERIVED FROM HER-2/NEU

CROSS-REFERENCE

This application is a continuation application of International Application No. PCT/IB2018/001428 filed Nov. 21, 2018, claims the benefit of U.S. Provisional Application No. 62/590,326 filed Nov. 23, 2017, which application is incorporated herein by reference.

SEQUENCE LISTING

The instant application contains a Sequence Listing which has been submitted electronically in ASCII format and is hereby incorporated by reference in its entirety. Said ASCII copy, created on Feb. 28, 2019, is named 56825-701_301_SL.txt and is 16,111 bytes in size.

SUMMARY

Described herein are chimeric bacteriophage that comprise fusion proteins comprising a cancer antigen fused to a bacteriophage protein. Such bacteriophage are useful in the treatment or prophylaxis of cancer.

Described herein, in a certain aspect, is a fusion protein comprising a bacteriophage protein fused to a cancer antigen. In certain embodiments, the cancer antigen is derived from an oncogene. In certain embodiments, the oncogene is HER-2/neu. In certain embodiments, the cancer antigen is derived from a transmembrane domain of HER-2/neu. In certain embodiments, the cancer antigen consists of or comprises GP2. In certain embodiments, the cancer antigen consists of or comprises the amino acid sequence set forth in SEQ ID NO: 6. In certain embodiments, the cancer antigen consists of or comprises E75. In certain embodiments, the cancer antigen consists of or comprises the amino acid sequence set forth in SEQ ID NO: 8. In certain embodiments, the cancer antigen consists of or comprises AE37. In certain embodiments, the cancer antigen consists of or comprises the amino acid sequence set forth in SEQ ID NO: 10. In certain embodiments, the cancer antigen consists of or comprises an immunogenic cancer antigen of PD-L1. In certain embodiments, the cancer antigen consists of or comprises the amino acid sequences set forth in any one of SEQ ID NOs: 17, 18, or 19. In certain embodiments, the cancer antigen consists of or comprises an immunogenic cancer antigen of Folate Receptor a. In certain embodiments, the cancer antigen consists of or comprises the amino acid sequences set forth in any one of SEQ ID NOs: 20, 21, 22, 23, or 24. In certain embodiments, the cancer antigen consists of or comprises an immunogenic cancer antigen of MAGE. In certain embodiments, the cancer antigen consists of or comprises the amino acid sequences set forth in any one of SEQ ID NOs: 25 or 26. In certain embodiments, the bacteriophage is a λ phage. In certain embodiments, the bacteriophage is λ phage F7. In certain embodiments, the bacteriophage protein is a capsid protein. In certain embodiments, the capsid protein is GpD. In certain embodiments, the capsid protein consists of or comprises an amino acid sequence at least about 90%, 95%, 97%, 98%, 99% or 100% identical to the amino acid sequence set forth in SEQ ID NO: 2. In certain embodiments, the fusion protein further comprises a linker between the capsid protein and the cancer antigen. In certain embodiments, the linker consists of or comprises an amino acid sequence encoded by a nucleic acid sequence having at least about 90% identity to the sequence set forth in SEQ ID NO 3. In certain embodiments, the fusion protein consists of or comprises the amino acid sequence set forth in any one of SEQ ID NOs: 12, 14, or 16. In certain embodiments, described herein is a nucleic acid encoding the fusion protein. In certain embodiments, the nucleic acid comprises a nucleotide sequence with at least about 90%, 95%, 97%, 98%, 99%, or 100% sequence homology to a sequence selected from any one of SEQ ID NOs: 11, 13, and 15. In certain embodiments, described herein is a vector comprising the nucleic acid. In certain embodiments, described herein, is a host cell comprising the nucleic acid, or the vector, capable of producing the fusion protein. In certain embodiments, described herein, is a bacteriophage comprising the fusion protein. In certain embodiments, described herein, is a vaccine comprising the fusion protein and a pharmaceutically acceptable carrier. In certain embodiments, the vaccine further comprises an adjuvant. In certain embodiments, an adjuvant is not included with the vaccine. In certain embodiments, described herein, is a method of treating and/or preventing cancer in an individual, the method comprising administering the fusion protein, the bacteriophage, or the vaccine to the individual. In certain embodiments, the individual is a human. In certain embodiments, the cancer comprises breast cancer, ovarian cancer, lung cancer, pancreatic cancer, melanoma, or colon cancer. In certain embodiments, the breast cancer is triple negative breast cancer. In certain embodiments, described herein, is a method of inducing an anti-tumor T-cell response in an individual, the method comprising administering the fusion protein, the bacteriophage, or the vaccine to an individual. In certain embodiments, the individual is a human. In certain embodiments, the anti-tumor T-cell response is a CTL response. In certain embodiments, the anti-tumor T-cell response is a T helper response. In certain embodiments, described herein, is a method of immunizing an individual, the method comprising administering the fusion protein, the bacteriophage, or the vaccine to the individual. In certain embodiments, the individual is a human. In certain embodiments, the individual has not been diagnosed with a cancer, is not suspected of being afflicted with cancer, or has undergone one or more treatments for cancer. Also described herein is a use of the fusion protein of, the bacteriophage, or the vaccine for use in treating and/or preventing cancer in an individual. In certain embodiments, the individual is a human. In certain embodiments, the cancer comprises breast cancer, ovarian cancer, lung cancer, pancreatic cancer, melanoma, or colon cancer. In certain embodiments, the breast cancer is triple negative breast cancer. Also described herein is a use of the fusion protein, the bacteriophage, or the vaccine for immunizing an individual. In certain embodiments, the individual is a human. Also described herein is a use of the fusion protein, the bacteriophage, or the vaccine for inducing an anti-tumor T-cell response in an individual. In certain embodiments, the individual is a human. In certain embodiments, the anti-tumor T-cell response is a CTL response. In certain embodiments, the anti-tumor T-cell response is a T helper response. In certain embodiments, anti-tumor T-cell response is against an antigen set forth in any one of SEQ ID NOs: 6, 8, 10, 17, 18, 19, 20, 21, 22, 23, 24, 25, or 26.

The novel features of the present invention will become apparent to those of skill in the art upon examination of the following detailed description of the invention. It should be understood, however, that the detailed description of the invention and the specific examples presented, while indicating certain aspects of the present invention, are provided for illustration purposes only because various changes and modifications within the spirit and scope of the invention will become apparent to those of skill in the art from the detailed description of the invention and claims that follow.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The present invention will be further understood from the following description with reference to the Figures, in which:

FIG. 3A shows log-fold changes in gene expression compared with the TN buffer are expressed. FIG. 3B shows log-fold changes in gene expression compared with the λ F7 are expressed. β-actin was used to normalize gene expression level for each sample. All values represent means±SD (n=3). *P<0.001 and P<0.01; denotes significant difference from controls.

FIG. 5A shows data from tumor growth measured two times every week. FIG. 5B shows mouse survival data followed for 91 days. The data indicate mean±SEM (n=7). **P<0.01; denotes significant effects compared to the TN buffer group.

FIG. 6A shows a lambda capsid-cancer antigen fusion protein. FIG. 6B shows a plasmid comprising nucleotide sequence encoding a lambda capsid-cancer antigen fusion protein. Neither schematic is to scale.

DETAILED DESCRIPTION

Figure 1:
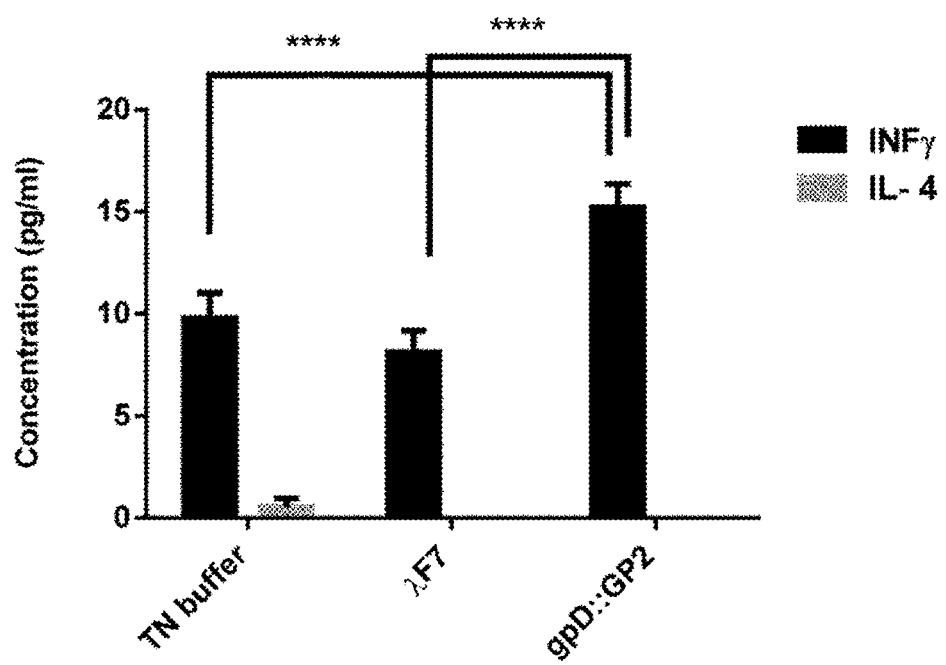
FIG. 1 shows cytokine production in gpD::GP2 display phage as demonstrated by ELISA. Mice were immunized with three booster doses of $10^8$ PFU gpD::GP2, the negative controls included $10^8$ PFU λ F7 or TN buffer. Two weeks after the last injection, sera from three mice from each group were harvested and concentrations of cytokines were evaluated using IFN-γ and IL-4 ELISA assay kits. Data are shown as mean±SEM. (n=3). ****P<0.0001; denotes significant difference from controls.

Described herein are chimeric bacteriophage that comprise fusion proteins comprising a cancer antigen fused to a bacteriophage protein. Such bacteriophage are useful in the treatment or prophylaxis of cancer.

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods and materials similar or equivalent to those described herein can be used in the practice for testing of the present invention, the typical materials and methods are described herein. In describing and claiming the present invention, the following terminology will be used.

It is also to be understood that the terminology used herein is for the purpose of describing particular aspects only, and is not intended to be limiting. Many patent applications, patents, and publications are referred to herein to assist in understanding the aspects described. Each of these references are incorporated herein by reference in their entirety.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Typically, a composition consisting essentially of a set of components will comprise less than 5% by weight, typically less than 3% by weight, more typically less than 1%, and even more typically less than 0.1% by weight of non-specified component(s).

It will be understood that any component defined herein as being included may be explicitly excluded from the claimed invention by way of proviso or negative limitation. For example, in a particular aspect, an adjuvant is explicitly excluded from the aspects described herein.

In addition, all ranges given herein include the end of the ranges and also any intermediate range points, whether explicitly stated or not.

Terms of degree such as "substantially", "about" and "approximately" as used herein mean a reasonable amount of deviation of the modified term such that the end result is not significantly changed. These terms of degree should be construed as including a deviation of ±10% of the modified term if this deviation would not negate the meaning of the word it modifies.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example." The word "or" is intended to include "and" unless the context clearly indicates otherwise.

A "vaccine" is a pharmaceutical composition that induces a prophylactic or therapeutic immune response in a subject. In some cases, the immune response is a protective immune response. Typically, a vaccine induces an antigen-specific immune response to an antigen of a pathogen or to a cellular constituent correlated with a pathological condition, such as cancer. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine induces an immune response that treats and/or prevents cancer as compared to a control.

The term "antigen" as used herein is defined as a molecule that provokes an immune response. This immune response may involve either antibody production, or the activation of specific immunologically-competent cells, such as T lymphocytes, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the aspects described herein include, but are not limited to, the use of partial nucleotide sequences of more than one gene and that these nucleotide sequences could be arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a cell, or a biological fluid.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" as used herein is defined as the transcription and/or translation of a particular nucleotide sequence driven by its promoter.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad.

Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The terms "therapeutically effective amount", "effective amount" or "sufficient amount" mean a quantity sufficient, when administered to a subject, including a mammal, for example a human, to achieve a desired result, for example an amount effective to cause a protective immune response. Effective amounts of the compounds described herein may vary according to factors such as the immunogen, age, sex, and weight of the subject. Dosage or treatment regimens may be adjusted to provide the optimum therapeutic response, as is understood by a skilled person. For example, administration of a therapeutically effective amount of the fusion proteins described herein is, in aspects, sufficient to increase immunity against cancer.

Moreover, a treatment regimen of a subject with a therapeutically effective amount may consist of a single administration, or alternatively comprise a series of applications. The length of the treatment period depends on a variety of factors, such as the immunogen, the age of the subject, the concentration of the agent, the responsiveness of the patient to the agent, or a combination thereof. It will also be appreciated that the effective dosage of the agent used for the treatment may increase or decrease over the course of a particular treatment regimen. Changes in dosage may result and become apparent by standard diagnostic assays known in the art. The fusion proteins described herein may, in aspects, be administered before, during or after treatment with conventional therapies for the disease or disorder in question, such as cancer.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The terms "individual," "subject," or "patient" are interchangeably used and refer to any mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human. In certain embodiments, the individual is a human individual. In certain embodiments, the human individual is suspected of being afflicted with cancer, or possesses a high risk of developing a cancer based upon a genetic, familial, or environmental risk factor. In certain embodiments, the individual possesses a mutated BRCA1 or BRCA2 gene. In certain embodiments, the individual has a mother, grandmother, aunt, or sibling that has been diagnosed with breast cancer.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

The term "adjuvant" refers to a compound or mixture that is present in a vaccine and enhances the immune response to an antigen present in the vaccine. For example, an adjuvant may enhance the immune response to a polypeptide present in an autologous cancer cell vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block copolymer adjuvants (e.g., CRL 1005), aluminum phosphates (e.g., AlPO$_4$), R-848 (a Th1-like adjuvant), imiquimod, PAM3CYS, poly (I:C), loxoribine, BCG (bacille Calmette-Guerin) and *Corynebacterium parvum*, CpG oligodeoxynucleotides (ODN), cholera toxin derived antigens (e.g., CTA 1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

"Active" or "activity" for the purposes herein refers to a biological and/or an immunological activity of the fusion proteins described herein, wherein "biological" activity refers to a biological function (either inhibitory or stimulatory) caused by the fusion proteins.

The fusion proteins described herein may include modifications. Such modifications include, but are not limited to, conjugation to an effector molecule such as an anti-cancer agent or an adjuvant. Modifications further include, but are not limited to conjugation to detectable reporter moieties. Modifications that extend half-life (e.g., pegylation) are also included. Proteins and non-protein agents may be conjugated to the fusion proteins by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990), which is incorporated by reference herein and those described by Amon et al., Adv. Exp. Med. Biol. 303, 79-90 (1991) and by Kiseleva et al, Mol. Biol. (USSR)25, 508-514 (1991), both of which are incorporated by reference herein.

Figure 6A:
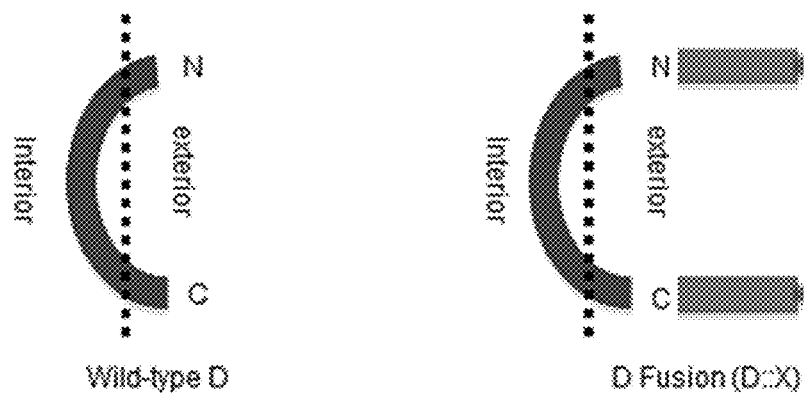
FIGS. 6A-6B show a simplified schematic of a bacteriophage capsid protein fused to a cancer antigenic peptide and a vector used to produce the bacteriophage.

Fusion Proteins and Bacteriophagies,

Described herein are fusion proteins. The fusion proteins comprise a bacteriophage protein fused to a cancer antigen. FIG. 6A illustrates a certain non-limiting embodiment of a bacteriophage protein fused to a cancer antigen. In this depiction a capsid protein comprises a cancer antigen fused to the N- or C-terminus of a capsid protein, optionally this fusion comprises a polypeptide linker between the capsid protein and the cancer antigen. In certain embodiments, the cancer antigen is fused to the C-terminus. In certain embodiments, the cancer antigen is fused to the N-terminus. In certain embodiments, the cancer antigen is fused to the N-terminus and the C-terminus. In certain embodiments, the cancer antigen can be the same antigen fused to both the N-terminus and the C-terminus. In certain embodiments, the cancer antigen can be a different antigen fused to the N-terminus than is fused to the C-terminus.

The cancer antigen may be any antigen that has the potential to elicit a protective immune response against the cancer in question. Cancer antigens are known and are described in, for example, U.S. Patent Application Publication No. US 2007/0020232, which is incorporated herein by reference in its entirety. Non-limiting examples include oncogenes and tumor suppressor genes, and specific cancer antigens contemplated for use herein include short peptide sequences derived from MUC-1, mutant B-raf, HER-2/neu, EGFR (variants 1-4), VEGFR (variants 1-2), folate receptor a, PSA, PSMA, GP-100, CEA, CA 19.9, MART-1, K-ras, N-ras, H-ras, PD-L1, melanoma antigen gene (MAGE), or p53. In certain embodiments, the cancer antigen is an immunogenic antigen of HER-2/neu. In certain embodiments, the cancer antigen comprises or consists of GP2 (SEQ ID NO: 6), E75 (SEQ ID NO: 8), and/or AE37 (SEQ ID NO: 10). In certain embodiments, the cancer antigen is an immunogenic antigen of PD-L1. In certain embodiments, the cancer antigen is an immunogenic antigen of folate receptor a. In certain embodiments, the cancer antigen is an immunogenic antigen of melanoma antigen gene (MAGE). In certain embodiments, the immunogenic antigen of PD-L1 comprises or consists of FMTYWHLLNAFTVTVPKDL (SEQ ID NO: 17), VILGAILLCLGVALTFIFRLRKG (SEQ ID NO: 18), or LLNAFTVTV (SEQ ID NO: 19). In certain embodiments, the immunogenic antigen of folate receptor a comprises or consists of RTELLNVCMNAKHHKEK (SEQ ID NO: 20), QCRPWRKNACCSTNT (SEQ ID NO: 21), QCRPWRKNACCSTNT (SEQ ID NO: 22), LGP-WIQQVDQSWRKERV (SEQ ID NO: 23), or PWAAWP-FLLSLALMLLWL (SEQ ID NO: 24). In certain embodiments, the immunogenic antigen of the melanoma antigen gene (MAGE) comprises or consists of EADPTGHSY (SEQ ID NO: 25), or GLYDGMEHL (SEQ ID NO: 26).

The cancer antigens useful for inclusion into the bacteriophage fusion proteins are immunogenic antigens. An immunogenic antigen is one that elicits an immune response in B cells or T cells of an individual when properly immunized. The antigens described herein exhibit major histocompatibility class (MHC) restriction. In humans, MHC are also known as human leukocyte antigens (HLA). There are two main types of MHC, Class I (MHC class I) and Class II (MHC class II). Immunogenic antigens that are MHC class I restricted will bind MHC class I molecules, and generally comprise antigens between 8 and 11 amino acids in length. Immunogenic antigens that are MHC class II restricted will bind MHC class II molecules, and generally comprise antigens greater than 12 amino acids in length. In certain embodiments, the cancer antigen is restricted or binds to a human leukocyte antigen (HLA). In certain embodiments, the cancer antigen is restricted or binds to human MHC class I. In certain embodiments, the cancer antigen is restricted or binds to human MHC class II.

It will be understood that the cancer antigens described herein may be used singly or in any combination, such that different fusion proteins linked to different antigens may be combined together in a single composition, such that a resultant bacteriophage may comprise a plurality of different cancer antigens. In addition, different bacteriophages, each comprising a single cancer antigen, may be combined together in a composition or used separately in a combined treatment method. In certain embodiments, the fusion protein comprises a bacteriophage protein and a plurality of 2, 3, 4, 5, 6, 7, 8, 9, or 10 of the same cancer antigen. In certain embodiments, the fusion protein comprises a bacteriophage protein and a plurality of 2, 3, 4, 5, 6, 7, 8, 9, or 10 different cancer antigens. In certain embodiments, the cancer antigens are separated by linkers. In certain embodiments, the fusion proteins are expressed by a bacteriophage.

The bacteriophage protein may be from any known bacteriophage including, but not limited to, bacteriophages that belong to any of the following virus families: Corticoviridae, Cystoviridae, Inoviridae, Leviviridae, Microviridae, Myoviridae, Podoviridae, Siphoviridae, or Tectiviridae. The bacteriophage may be a lytic bacteriophage or a lysogenic bacteriophage. A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells. A lysogenic bacteriophage is one capable of entering the lysogenic pathway, in which the bacteriophage becomes a dormant, passive part of the cell's genome through prior to completion of its lytic cycle.

Typically, the bacteriophage protein is derived from a bacteriophage of the family Siphoviridae and is more typically phage λ. In typical aspects, the bacteriophage is phage λF7, which has a mutation in the gpD gene resulting in a truncated gpD fragment when translated in a wild type (non-suppressor) host and a functional gpD protein when the phage is propagated in an amber suppressor strain of $E.\ coli$ or when function D is expressed in trans. Typically, the bacteriophage protein is a capsid protein and, typically, the capsid protein is gpD. This is because gpD is tolerant of peptide fusions at either end and is capable of high capacity display.

In certain embodiments, the bacteriophage protein is from a lambdoid phage. In certain embodiments, the lambdoid phage comprises phage 21, 434, 933W, λ, λvir, φ27, φ80, φ82, φKO2, φE125, D3, Gifsy-1, Gifsy-2, H-19B, HB-4, HK97, HK022, Fels-1, N15, P22, PA-2, PY54, Sf6, ST64T, SfV, or VT2-Sa. In certain embodiments, the lambdoid phage comprises phage λ.

In other aspects, the bacteriophage protein is derived from phage T2, T3, T4, T7, aT3/T7 recombinant phage, phage MS2, phage Qβ, or filamentous phages such as phage Ff, f1 or phage M13. Typical examples include phage T4 Hoc or Soc, or phage M13 pIII.

In certain aspects, the fusion proteins described herein comprise a flexible linker between the bacteriophage protein and the cancer antigen. This linker allows the antigen to adopt a favorable conformation once the protein is expressed.

The linker is generally long enough to impart some flexibility to the cancer antigen, although it will be understood that linker length will vary depending upon the bacteriophage protein and cancer antigen sequences and the three-dimensional conformation of the fusion protein. Thus, the linker is typically from about 1 to about 30 amino acid residues, such as from about 1, 2, 3, 4, 5, 6, 7, 8, 9, 10, 11, 12, 13, 14, 15, 16, 17, 18, 19, 20, 21, 22, 23, 24, 25, 26, 27, 28, or 29 to about 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues, such as from about 10 to about 18 amino acid residues, such as 10, 11, 12, 13, 14, 15, 16, 17, or 18 amino acid residues.

The linker may be of any amino acid sequence that does not interfere with immunogenicity of the cancer antigen. In one typical example, the flexible linker comprises a GG and/or GS repeat and, more typically, the flexible linker comprises the sequence TSGSGSGSGSGSG. In other aspects, the linker comprises or consists of an amino acid sequence encoded by a nucleic acid sequence having at least about 90%, 95%, 97%, 98%, 99%, or 100% identity to the sequence ACTAGCGGGTTCTGGTTCCGGTTCTGGTTCCGGTTCTGGC (SEQ ID NO: 3), or a fragment thereof.

In further aspects, a nucleic acid encoding the cancer antigen and the bacteriophage protein comprises an endonuclease cleavage site between the bacteriophage protein and the cancer antigen, such as a Kpn1 restriction site for simplified cloning of translational fusions. For example, the nucleic acid encoding the bacteriophage protein, linker, and/or cancer antigen may include a cleavage site in order to impart some modularity to the fusion protein, in that different cancer antigens, linkers, and/or bacteriophage proteins may be removed or added to the fusion protein as needed.

In certain embodiments, the fusion protein is a gpD-antigen protein, or optionally, a gpD-linker-antigen protein. In certain embodiments, the fusion protein comprises an amino acid sequence at least about 90%, 95%, 97%, 98%, or 99% identical to the amino acid sequence set forth in SEQ ID NO: 12. In certain embodiments, the fusion protein comprises the amino acid sequence set forth in SEQ ID NO: 12. In certain embodiments, the fusion protein comprises an amino acid sequence at least about 90%, 95%, 97%, 98%, or 99% identical to the amino acid sequence set forth in SEQ ID NO: 14. In certain embodiments, the fusion protein comprises the amino acid sequence set forth in SEQ ID NO: 14. In certain embodiments, the fusion protein comprises an amino acid sequence at least about 90%, 95%, 97%, 98%, or 99% identical to the amino acid sequence set forth in SEQ ID NO: 16. In certain embodiments, the fusion protein comprises the amino acid sequence set forth in SEQ ID NO: 16.

Figure 6B:
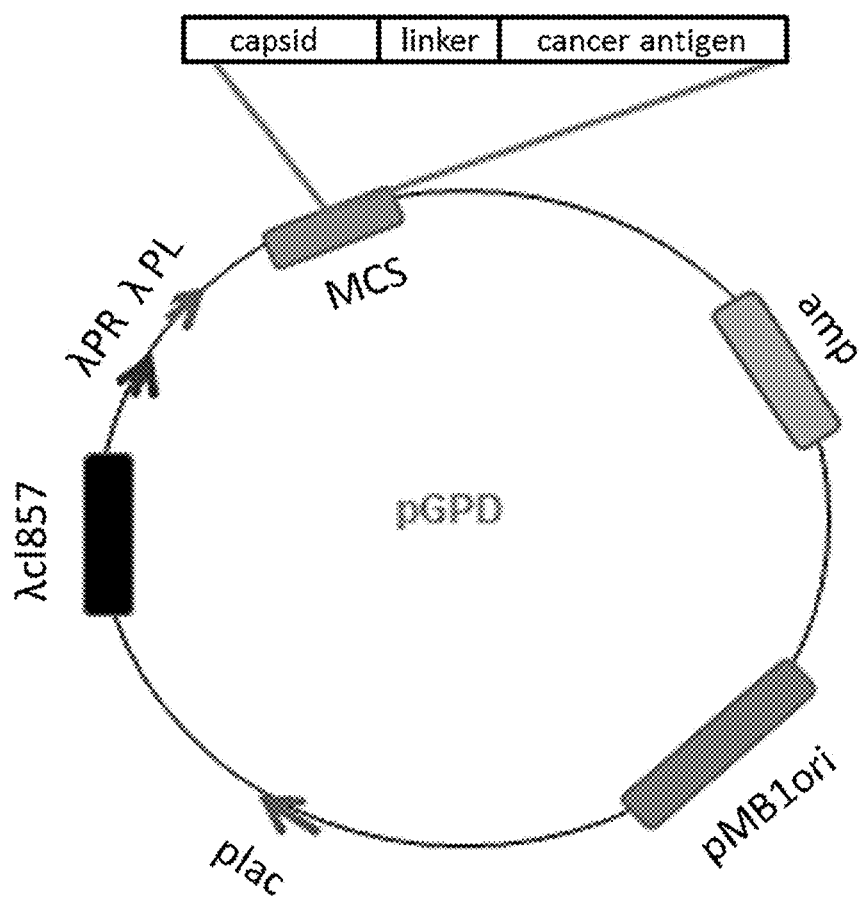

The fusion proteins described herein can be encoded by a nucleic acid comprising a nucleotide sequence encoding the fusion protein. In certain embodiments, the nucleic acid sequence is contained on a plasmid or other suitable vector. FIG. 6B shows a non-limiting embodiment of a plasmid that can be used to encode a fusion protein described herein. This plasmid can be utilized in a method of making a bacteriophage comprising a bacteriophage protein-cancer antigen fusion. In certain embodiments, the fusion protein is encoded by a nucleic acid comprising a nucleotide sequence having at least about 90%, 95%, 97%, 98%, or 99% homology to SEQ ID NO: 11. In certain embodiments, the fusion protein is encoded by a nucleic acid comprising the nucleotide sequence of SEQ ID NO: 11. In certain embodiments, the fusion protein is encoded by a nucleic acid comprising a nucleotide sequence having at least about 90%, 95%, 97%, 98%, or 99% homology to SEQ ID NO: 13. In certain embodiments, the fusion protein is encoded by a nucleic acid comprising the nucleotide sequence of SEQ ID NO: 13. In certain embodiments, the fusion protein is encoded by a nucleic acid comprising a nucleotide sequence having at least about 90%, 95%, 97%, 98%, or 99% homology to SEQ ID NO: 15. In certain embodiments, the fusion protein is encoded by a nucleic acid comprising the nucleotide sequence of SEQ ID NO: 15. In certain embodiments, a nucleotide sequence encoding a fusion protein is operably linked to regulatory elements that allow for selection, expression, and purification of the fusion protein.

The fusion proteins described herein may be expressed or displayed by a bacteriophage. When the fusion protein is expressed by a bacteriophage, the bacteriophage may act as an adjuvant reducing or eliminating the need for additional adjuvants. In certain embodiments, the fusion protein is expressed or displayed by a lambdoid phage. In certain embodiments, the lambdoid phage comprises phage 21, 434, 933W, λ, λvir, φ27, φ80, φ82, φKO2, φE125, D3, Gifsy-1, Gifsy-2, H-19B, HB-4, HK97, HK022, Fels-1, N15, P22, PA-2, PY54, Sf6, ST64T, SfV, or VT2-Sa. In certain embodiments, the lambdoid phage comprises phage λ. In other embodiments, the fusion protein is expressed by phage T2, T3, T4, T7, aT3/T7 recombinant phage, phage MS2, phage Qβ, or filamentous phages such as phage Ff, fl or phage M13. Typical examples include phage T4 Hoc or Soc, or phage M13 plll.

In certain embodiments, the fusion protein comprises a fusion of gpD and a cancer antigen, and is expressed or displayed by a lambdoid phage. In certain embodiments, the lambdoid phage comprises phage 21, 434, 933W, λ, λvir, φ27, φ80, φ82, φKO2, 4E125, D3, Gifsy-1, Gifsy-2, H-19B, HB-4, HK97, HK022, Fels-1, N15, P22, PA-2, PY54, Sf6, ST64T, SfV, or VT2-Sa. In certain embodiments, the lambdoid phage comprises phage λ. In other embodiments, the fusion protein is expressed by phage T2, T3, T4, T7, aT3/T7 recombinant phage, phage MS2, phage Qβ, or filamentous phages such as phage Ff, fl or phage M13. Typical examples include phage T4 Hoc or Soc, or phage M13 plll.

In certain embodiments, the fusion protein comprises a fusion of gpD and a cancer antigen comprising an immunogenic antigen of HER-2/Neu, PD-L1, folate receptor a, or MAGE, and the fusion protein is expressed or displayed by a lambdoid phage. In certain embodiments, the lambdoid phage comprises phage 21, 434, 933W, λ, λvir, φ27, φ80, φ82, φKO2, φE125, D3, Gifsy-1, Gifsy-2, H-19B, HB-4, HK97, HK022, Fels-1, N15, P22, PA-2, PY54, Sf6, ST64T, SfV, or VT2-Sa. In certain embodiments, the lambdoid phage comprises phage λ. In other embodiments, the fusion protein is expressed by phage T2, T3, T4, T7, aT3/T7 recombinant phage, phage MS2, phage Qβ, or filamentous phages such as phage Ff, fl or phage M13. Typical examples include phage T4 Hoc or Soc, or phage M13 plll.

The fusion proteins described herein may also comprise additional sequences to aid in their expression, detection or purification. Any such sequences or tags known to those of skill in the art may be used. For example, and without wishing to be limiting, the fusion proteins may comprise a targeting or signal sequence (for example, but not limited to ompA), a detection tag, exemplary tag cassettes include Strep tag, or any variant thereof, see, e.g., U.S. Pat. No. 7,981,632, incorporated herein by reference, His tag, Flag tag having the sequence motif DYKDDDDK, Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof, a purification tag (for example, but not limited to a $His_5$ or $His_6$), or a combination thereof.

In another example, the additional sequence may be a biotin recognition site such as that described by Cronan et al in WO 95/04069 or Voges et al in WO/2004/076670, both of which are incorporated herein by reference in their entireties. As is also known to those of skill in the art, linker sequences may be used in conjunction with the additional sequences or tags.

Also encompassed herein are isolated or purified fusion proteins, polypeptides, or fragments thereof immobilized onto a surface using various methodologies; for example, and without wishing to be limiting, the polypeptides may be linked or coupled to the surface via His-tag coupling, biotin binding, covalent binding, adsorption, and the like. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, a film, or any other useful surface.

In other aspects, the fusion proteins may be linked to a cargo molecule; the fusion proteins may deliver the cargo molecule to a desired site and may be linked to the cargo molecule using any method known in the art (recombinant technology, chemical conjugation, chelation, etc.). The cargo molecule may be any type of molecule, such as a therapeutic or diagnostic agent. For example, and without wishing to be limiting in any manner, the therapeutic agent may be a radioisotope, which may be used for radioimmunotherapy; a toxin, such as an immunotoxin; a cytokine, such as an immunocytokine; a cytotoxin; an apoptosis inducer; an enzyme; or any other suitable therapeutic molecule known in the art. In the alternative, a diagnostic agent may include, but is by no means limited to a radioisotope, a paramagnetic label such as gadolinium or iron oxide, a fluorophore, a Near Infra-Red (NIR) fluorochrome or dye (such as Cy3, Cy5.5, Alexa680, Dylight680, or Dylight800), an affinity label (for example biotin, avidin, etc), fused to a detectable protein-based molecule, or any other suitable agent that may be detected by imaging methods. In a specific, non-limiting example, the fusion protein may be linked to a fluorescent agent such as FITC or may genetically be fused to the Enhanced Green Fluorescent Protein (EGFP).

Methods

The fusion proteins and bacteriophages described herein are useful for the prophylactic vaccination or treatment of cancer. In certain embodiments, the cancer is any cancer expressing HER-2/neu. In certain embodiments, the cancer is any cancer expressing PD-L1. In certain embodiments, the cancer is any cancer expressing MAGE. In certain embodiments, the cancer is any cancer expressing folate receptor a. In certain embodiments, the cancer comprises breast cancer, ovarian cancer, lung cancer, pancreatic cancer, melanoma, or colon cancer. In certain embodiments, the cancer comprises triple negative breast cancer.

The fusion proteins and bacteriophages described herein are useful for inducing an anti-tumor T cell response. In certain embodiments, the T cell response is specific for HER-2/neu. In certain embodiments, the T cell response is specific for PD-L1. In certain embodiments, the T cell response is specific for MAGE. In certain embodiments, the T cell response is specific for folate receptor a. In certain embodiments, the T cell response is specific for any of SEQ ID NOs: 6, 8, 10, 17, 18, 19, 20, 21, 22, 23, 24, 25, or 26. In certain embodiments, the T cell response is a CD4+ T cell response. In certain embodiments, the T cell response is a CD8+ T cell response. T cell responses can be suitably measured using an assay such as tetramer staining, a mixed lymphocyte reaction, cytokine release in response to antigen restimulation, proliferation in response to antigen restimulation, or cytotoxic killing in response to antigen restimulation.

Any suitable method or route can be used to administer the fusion proteins or bacteriophages described herein. Routes of administration include, for example, oral, inhaled, intravenous, intraperitoneal, subcutaneous, or intramuscular administration. In certain embodiments, the fusion proteins or bacteriophages can be administered parenterally. In certain embodiments, the fusion proteins or bacteriophages described herein are administered subcutaneously. In certain embodiments, the fusion proteins or bacteriophages described herein are administered intramuscularly. In certain embodiments, the fusion proteins or bacteriophages described herein are administered rectally. In certain embodiments, the fusion proteins or bacteriophages described herein are administered orally. In certain embodiments, the fusion proteins or bacteriophages described herein are administered intratumoral. In certain embodiments, the fusion proteins or bacteriophages described herein are administered intravenously.

In another aspect, described herein are methods of inducing an anti-tumor T cell response in an individual. The response may be induced prophylactically, that is before an individual is suspected of being afflicted with cancer, or therapeutically, that is after an individual is suspected of being afflicted with a cancer. Depending upon the exact antigen the T cell response may be a T helper response, comprised of CD4+ T cells, or a cytotoxic T-lymphocyte (CTL) response, comprised of CD8+ T cells. In certain embodiments, the method comprises administering a composition comprising a fusion protein comprising a bacteriophage protein coupled to a cancer antigen to an individual. In certain embodiments, the method comprises administering a composition comprising a bacteriophage comprising a fusion protein comprising a bacteriophage protein coupled to a cancer antigen to an individual.

In another aspect, described herein are methods of treating individuals with cancer by administering a therapeutically effective amount of the fusion proteins or bacteriophages described herein to an individual in need thereof. Therapeutically effective means an amount effective to produce the desired therapeutic effect, such as providing a protective immune response against the antigen in question. Treating refers to ameliorating one or more pathological aspects of cancer and can comprise reducing tumor growth, inhibiting metastasis, reducing tumor burden, extending progression free survival, or extending overall life span. In certain embodiments, the method comprises, administering a composition comprising, a fusion protein comprising a bacteriophage protein coupled to a cancer antigen to an individual. In certain embodiments, the method comprises, administering a composition comprising, a bacteriophage comprising a fusion protein comprising a bacteriophage protein coupled to a cancer antigen to an individual.

A suitable dose can be administered to an individual for therapeutic purposes. Therapeutic immunization is employed in an individual diagnosed with or suspected of being afflicted with a cancer. In certain embodiments, a dose of a bacteriophage comprising a cancer antigen suitable for therapeutic administration comprises a dose of bacteriophage equivalent to between about 10 micrograms to about 10 milligrams of cancer antigen. In certain embodiments, a dose of a bacteriophage comprising a cancer antigen suitable for therapeutic administration comprises a dose of bacteriophage equivalent to between about 100 micrograms to about 10 milligrams of cancer antigen, between about 10 micrograms to about 1 milligram of cancer antigen, or between about 100 micrograms to about 1 milligram of cancer antigen. In certain embodiments, a dose of a bacteriophage comprising a cancer antigen suitable for therapeutic administration comprises a dose of bacteriophage equivalent to at least about 10, 50, 100, 200, 300, 400, 500, 600, 700, 800, or 900 micrograms of cancer antigen. In certain embodiments, a dose of a bacteriophage comprising a cancer antigen suitable for therapeutic administration comprises a dose of bacteriophage equivalent to at least about 1, 5, 10, 20, 30, 40, 50, 60, 70, 80, 90, or 100 milligrams of cancer antigen. In certain embodiments, a dose of a bacteriophage comprising a cancer antigen suitable for therapeutic administration comprises a dose of bacteriophage equivalent to no more than about, 50, 100, 200, 300, 400, 500, 600, 700, 800, or 900 micrograms of cancer antigen. In certain embodiments, a dose of a bacteriophage comprising a cancer antigen suitable for therapeutic administration comprises a dose of bacteriophage equivalent no more than about 1, 5, 10, 20, 30, 40, 50, 60, 70, 80, 90, or 100 milligrams of cancer antigen. In certain embodiments, a dose of a bacteriophage comprising a cancer antigen suitable for therapeutic administration comprises a dose of bacteriophage equivalent to about, 50, 100, 200, 300, 400, 500, 600, 700, 800, or 900 micrograms of cancer antigen. In certain embodiments, a dose of a bacteriophage comprising a cancer antigen suitable for therapeutic administration comprises a dose of bacteriophage equivalent to about 1, 5, 10, 20, 30, 40, 50, 60, 70, 80, 90, or 100 milligrams of cancer antigen.

When an isolated bacteriophage protein cancer antigen fusion protein is administered for therapeutic purposes the dose can comprise between about 10 micrograms to about 10 milligrams of cancer antigen. In certain embodiments, a dose of bacteriophage protein cancer antigen fusion protein is between about 100 micrograms to about 10 milligrams of cancer antigen, between about 10 micrograms to about 1 milligram of cancer antigen, or between about 100 micrograms to about 1 milligram of cancer antigen. In certain embodiments, a dose of bacteriophage protein cancer antigen fusion protein is at least about 10, 50, 100, 200, 300, 400, 500, 600, 700, 800, or 900 micrograms. In certain embodiments, a dose of bacteriophage protein cancer antigen fusion protein is least about 1, 5, 10, 20, 30, 40, 50, 60, 70, 80, 90, or 100 milligrams. In certain embodiments, a dose of bacteriophage protein cancer antigen fusion protein is no more than about, 50, 100, 200, 300, 400, 500, 600, 700, 800, or 900 micrograms. In certain embodiments, a dose of bacteriophage protein cancer antigen fusion protein is no more than about 1, 5, 10, 20, 30, 40, 50, 60, 70, 80, 90, or 100 milligrams. In certain embodiments, a dose of bacteriophage protein cancer antigen fusion protein is about, 50, 100, 200, 300, 400, 500, 600, 700, 800, or 900 micrograms. In certain embodiments, a dose of bacteriophage protein cancer antigen fusion protein is about 1, 5, 10, 20, 30, 40, 50, 60, 70, 80, 90, or 100 milligrams.

In another aspect, described herein are methods of vaccinating individuals against cancer by administering a prophylactically effective amount of the fusion proteins or bacteriophages described herein to an individual in need thereof. In certain embodiments, the method comprises, administering a composition comprising, a fusion protein comprising a bacteriophage protein coupled to a cancer antigen to an individual. In certain embodiments, the method comprises, administering a composition comprising, a bacteriophage comprising a fusion protein comprising a bacteriophage protein coupled to a cancer antigen to an individual.

A suitable dose can be administered to an individual for prophylactic immunization. Prophylactic immunization is employed in individuals who are not currently diagnosed with or suspected of having cancer, or who may be in remission from cancer. In certain embodiments, a dose of a bacteriophage comprising a cancer antigen suitable for prophylactic administration comprises a dose of bacteriophage equivalent to between about 10 micrograms to about 10 milligrams of cancer antigen. In certain embodiments, a dose of a bacteriophage comprising a cancer antigen suitable for prophylactic administration comprises a dose of bacteriophage equivalent to between about 100 micrograms to about 10 milligrams of cancer antigen, between about 10 micrograms to about 1 milligram of cancer antigen, or between about 100 micrograms to about 1 milligram of cancer antigen. In certain embodiments, a dose of a bacteriophage comprising a cancer antigen suitable for prophylactic administration comprises a dose of bacteriophage equivalent to at least about 10, 50, 100, 200, 300, 400, 500, 600, 700, 800, or 900 micrograms of cancer antigen. In certain embodiments, a dose of a bacteriophage comprising a cancer antigen suitable for prophylactic administration comprises a dose of bacteriophage equivalent to at least about 1, 5, 10, 20, 30, 40, 50, 60, 70, 80, 90, or 100 milligrams of cancer antigen. In certain embodiments, a dose of a bacteriophage comprising a cancer antigen suitable for prophylactic administration comprises a dose of bacteriophage equivalent to no more than about, 50, 100, 200, 300, 400, 500, 600, 700, 800, or 900 micrograms of cancer antigen. In certain embodiments, a dose of a bacteriophage comprising a cancer antigen suitable for prophylactic administration comprises a dose of bacteriophage equivalent no more than about 1, 5, 10, 20, 30, 40, 50, 60, 70, 80, 90, or 100 milligrams of cancer antigen. In certain embodiments, a dose of a bacteriophage comprising a cancer antigen suitable for prophylactic administration comprises a dose of bacteriophage equivalent to about, 50, 100, 200, 300, 400, 500, 600, 700, 800, or 900 micrograms of cancer antigen. In certain embodiments, a dose of a bacteriophage comprising a cancer antigen suitable for prophylactic administration comprises a dose of bacteriophage equivalent to about 1, 5, 10, 20, 30, 40, 50, 60, 70, 80, 90, or 100 milligrams of cancer antigen.

When an isolated bacteriophage protein cancer antigen fusion protein is administered for prophylactic purposes the dose can comprise between about 10 micrograms to about 10 milligrams of cancer antigen. In certain embodiments, a dose of bacteriophage protein cancer antigen fusion protein is between about 100 micrograms to about 10 milligrams of cancer antigen, between about 10 micrograms to about 1 milligram of cancer antigen, or between about 100 micrograms to about 1 milligram of cancer antigen. In certain embodiments, a dose of bacteriophage protein cancer antigen fusion protein is at least about 10, 50, 100, 200, 300, 400, 500, 600, 700, 800, or 900 micrograms. In certain embodiments, a dose of bacteriophage protein cancer antigen fusion protein is least about 1, 5, 10, 20, 30, 40, 50, 60, 70, 80, 90, or 100 milligrams. In certain embodiments, a dose of bacteriophage protein cancer antigen fusion protein is no more than about, 50, 100, 200, 300, 400, 500, 600, 700, 800, or 900 micrograms. In certain embodiments, a dose of bacteriophage protein cancer antigen fusion protein is no more than about 1, 5, 10, 20, 30, 40, 50, 60, 70, 80, 90, or 100 milligrams. In certain embodiments, a dose of bacteriophage protein cancer antigen fusion protein is about, 50, 100, 200, 300, 400, 500, 600, 700, 800, or 900 micrograms. In certain embodiments, a dose of bacteriophage protein cancer antigen fusion protein is about 1, 5, 10, 20, 30, 40, 50, 60, 70, 80, 90, or 100 milligrams.

For prophylactic immunization multiple doses can be given, with subsequent doses providing a boost. When multiple doses are given doses of bacteriophage comprising a cancer antigen can be used to prime, and isolated bacteriophage protein cancer antigen fusion protein can be administered as a booster immunization. This booster immunization can be repeated 1, 2, 3, 4, 5, 6, 7, 8, 9, 10 or more times. The booster can be administered weekly, monthly or annually.

It is understood that the fusion proteins or bacteriophages described herein, where used in an individual for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the individual. In certain embodiments, if a bacteriophage comprising a cancer antigen is administered as an inactivated bacteriophage. "Inactivated" means not capable of replication in a suitable host. In certain embodiments, if a bacteriophage comprising a cancer antigen is administered as a live bacteriophage. "Live" means capable of replication in a suitable host.

Although the fusion proteins described herein are particularly useful for administration to humans, they may be administered to other mammals as well. The term "mammal" as used herein is intended to include, but is not limited to, humans, laboratory animals, domestic pets and farm animals.

Figure 7:
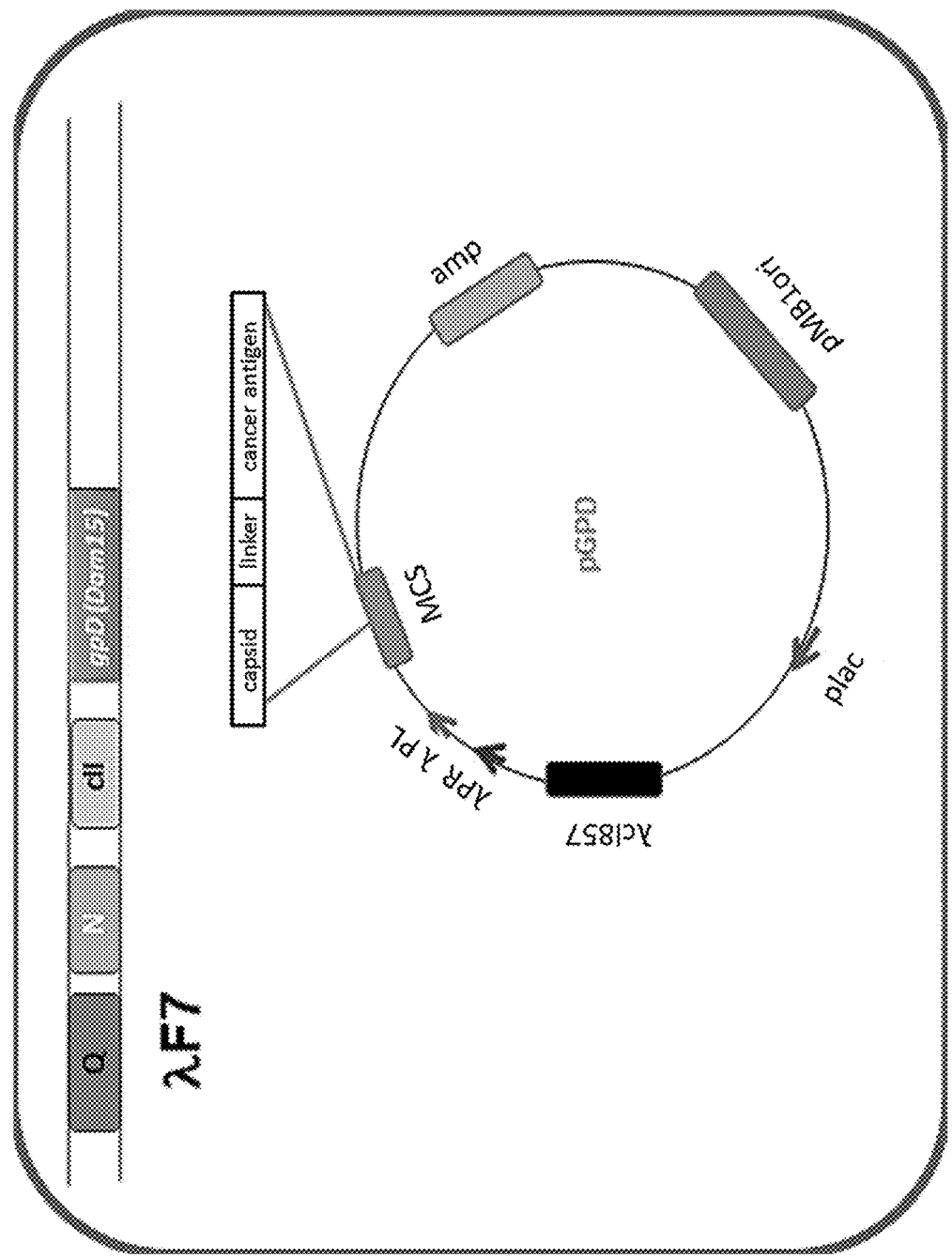
FIG. 7 depicts a prokaryotic cell for producing a bacteriophage comprising a lambda capsid-cancer antigen fusion protein encoding plasmid. This schematic not to scale.

In certain aspects described herein is a cell or population of cells comprising a vector comprising a nucleic acid encoding a bacteriophage protein-cancer antigen fusion protein. FIG. 7 shows such a configuration the cell can comprise all genes necessary for phage production and lack a bacteriophage protein that can be supplied by an exogenous vector or plasmid. In certain embodiments, the cell or population of cells is a prokaryotic cell. In certain embodiments, the cell or population of cells is E. coli. In certain embodiments, the bacteriophage protein is a capsid protein. In certain embodiments, the cell or population of cells is E. coli. In certain embodiments, the bacteriophage protein is a gpD capsid protein.

In certain aspects, described herein, are methods of making a therapeutic cancer treatment comprising incubating a plurality of prokaryotic cells, the prokaryotic cells comprising a nucleic acid comprising a nucleotide sequence that encodes a fusion protein, the fusion protein comprising a bacteriophage protein coupled to a cancer antigen, under conditions sufficient for expression and assembly of a bacteriophage comprising the fusion protein in the prokaryotic cell. In certain embodiments, the method further comprises lysing the prokaryotic cells. In certain embodiments, the method further comprises one or more purification steps after lysing the prokaryotic cells. In certain embodiments, the prokaryotic cell is an *E. coli* cell. In certain embodiments, the methods further comprise admixing the bacteriophage comprising the fusion protein and a pharmaceutically acceptable carrier. In certain embodiments, the bacteriophage protein is a capsid protein. In certain embodiments, the cell or population of cells is *E. coli*. In certain embodiments, the bacteriophage protein is a gpD capsid protein.

In certain aspects, described herein, are methods of making a prophylactic cancer vaccine comprising incubating a plurality of prokaryotic cells, the prokaryotic cells comprising a nucleic acid comprising a nucleotide sequence that encodes a fusion protein, the fusion protein comprising a bacteriophage protein coupled to a cancer antigen, under conditions sufficient for expression and assembly of a bacteriophage comprising the fusion protein in the prokaryotic cell. In certain embodiments, the method further comprises lysing the prokaryotic cells. In certain embodiments, the method further comprises one or more purification steps after lysing the prokaryotic cells. In certain embodiments, the prokaryotic cell is an *E. coli* cell. In certain embodiments, the methods further comprise admixing the bacteriophage comprising the fusion protein and a pharmaceutically acceptable carrier. In certain embodiments, the bacteriophage protein is a capsid protein. In certain embodiments, the cell or population of cells is *E. coli*. In certain embodiments, the bacteriophage protein is a gpD capsid protein.

In certain aspects, described herein, are methods of making a composition for inducing an anti-tumor T cell response comprising incubating a plurality of prokaryotic cells, the prokaryotic cells comprising a nucleic acid comprising a nucleotide sequence that encodes a fusion protein, the fusion protein comprising a bacteriophage protein coupled to a cancer antigen, under conditions sufficient for expression and assembly of a bacteriophage comprising the fusion protein in the prokaryotic cell. In certain embodiments, the method further comprises lysing the prokaryotic cells. In certain embodiments, the method further comprises one or more purification steps after lysing the prokaryotic cell. In certain embodiments, the prokaryotic cell is an *E. coli* cell. In certain embodiments, the methods further comprise admixing the bacteriophage comprising the fusion protein and a pharmaceutically acceptable carrier.

Also included herein are kits for vaccination, comprising a therapeutically or prophylactically effective amount of a fusion protein or bacteriophage described herein. The kits can further contain any suitable adjuvant or implements for administration. Kits may include instructions.

The above disclosure generally describes the present invention. A more complete understanding can be obtained by reference to the following specific examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The following examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989), Molecular Cloning: A Laboratory Manual, 2nd edition, Cold Spring Harbor Laboratory Press, which is incorporated by reference herein.

Without further description, it is believed that one of ordinary skill in the art can, using the preceding description and the following illustrative examples, make and utilize the compounds of the present invention and practice the claimed methods.

EXAMPLES

The following working examples, specifically point out the typical aspects of the present invention, and are not to be construed as limiting in any way the remainder of the disclosure.

Generating a protective and long-lasting immune response is a primary goal in the expanding field of immunotherapeutic research. Described herein is an immunogenic vaccine delivery system to increase cytotoxic T lymphocyte (CTL) response against a breast cancer model over-expressing HER2/neu. Bacteriophage $\lambda$ displaying the HER2/neu derived peptide GP2 was constructed and used as an anticancer vaccine in a BALB/c mouse xenograft tumor model. Results indicated that phage nanoparticles displaying GP2 as a fused peptide to the gpD phage capsid protein induced a robust CTL response. Furthermore, the chimeric phage nanoparticles protected mice against HER-2-positive tumor challenge in both prophylactic and therapeutic settings. In conclusion, it is shown that $\lambda$ phage nanoparticles decorated with GP2 peptide are useful for the development of peptide-based vaccines against breast cancer.

Introduction

HER-2/neu is a proto-oncogene that is overexpressed in 20-35% of human breast cancers. The protein belongs to the human epidermal growth factor receptor (EGFR) family and is able to elicit both humoral and cellular immune responses in patients with breast and ovarian cancer. Immunogenic tumor cells produce multiple tumor-associated antigens (TAAs) and there is evidence that self-acting antitumor responses to TAAs may be repelled by the host's own immune system. Vaccines are designed to incite the intrinsic antitumor immune response by effectively presenting immunodominant TAAs and to stimulate a potent cytotoxic lymphocyte (CTL) immune response.

GP2 is a highly immunogenic peptide of interest against HER2/neu overexpressing breast cancers. This short peptide is derived from the HER-2/neu protein transmembrane domain (654-662: IISAWGIL) and is recognized by the endogenous immune system via MHC class I. Safe and efficient HER-2-specific immune responses were demonstrated in Phase I and II clinical trials with GP2, including a CD8+ cytotoxic T-lymphocyte (CTL) response. GP2 is an appropriate candidate for peptide vaccine trials and is capable of producing strong immunogenicity.

Bacteriophage Lambda ($\lambda$) is a temperate phage characterized by a double-stranded DNA genome of 48,502 bp that exclusively infects *Escherichia coli* (*E. coli*) and can either lysogenize or grow vegatively on its bacterial host, although lytic strains exist that are incapable of forming a stable lysogen. Phage $\lambda$ is preferable to other bacteriophages for protein or peptide display. It has been illustrated to stably display fusion proteins or peptides larger than a few amino acids on its capsid, with copies per virion that are of two to three orders of magnitude higher than filamentous phage display vectors. The capsid of $\lambda$ is made up of the two major proteins, gpE and gpD. Mikawa et al. (1996) determined that both the N and C termini of gpD are neither at the trimer interaction interface nor do they interact with the other major capsid protein gpE and that the terminal tolerance and capacity depends on the peptide or protein that is fused. Subsequent studies demonstrated that gpD is tolerant of peptide and protein genetic fusions at either its N- or C-termini without interfering with λ phage production. The λF7 phage has a mutation in gpD gene and results in a truncated gpD fragment when translated in a wild type (non-suppressor) host. Through this mutation, a functional gpD protein can be produced when the phage infects amber suppressor strains of E. coli or functional D is expressed in trans.

In this study, an amber suppressor strain of E. coli, λF7 (λDam15), was used for cloning of a cassette containing the capsid protein (gpD)-linker-polypeptide (GP2). This phage propagated in an amber suppressor strain where the D-fusion protein, gpD::GP2, was provided in trans from a multi-copy temperature-inducible expression plasmid (Sokolenko et al., 2012) that produces gpD::GP2 to complement for the Dam15 mutation of λ and decorate viable phage progeny. Both prophylactic and therapeutic administration of the GP2 displaying λ phage nanoparticles were assessed in a BALB/c mice model of breast cancer.

Materials and Methods
Bacterium and Phage Strains

For phage plating and amplification Escherichia coli strain BB4 (supF58 supE44 HsdR514 galK2 galT22 trpR55 metB1 tonA DE(lac) U169) was used. For construction of the λ vector the phage λ F7 (λimm21Dam15) was used. The plasmid pGPD, as a general purpose vector was used for cloning and expression of gpD fusion peptide. To produce the fusion peptide, the terminal stop codon from gpD was removed and an in-frame fusion with the GP2 sequence (Sense: 5'ATTATTAGCGCGGIGGIGGGCATTCTGTAG 3') (SEQ ID NO: 27) and (Anti-sense 3'TAATAATCGCGC-CACCACCCGTAAGACATC 5') (SEQ ID NO: 28) was created.

The two fragments were separated by an in-frame short linker (ACTAGCGGGTTCTGGTTCCGGTTCTGGTTC-CGGTTCTGGC) (SEQ ID NO: 3) that was placed between and followed by a Kpn1 cut site to maximize fusion functionality and also allow for additional fusions to be designed in the future. The gpD::GP2 sequence was then amplified and cloned into the Hpa1 and Nco1 sites on pGPD, placing it under the control of the $P_L$ strong promoter that is regulated by the temperature-inducible repressor, CI857, conferring temperature-regulated expression.

Phage Amplification and Purification

Cultures of transformed Sup⁺ (SupE) (pD::GP2) E. coli cells were grown on plates at 37° C. overnight. Dilutions of primary lysates (1:1000) were prepared in 10 μL of TN buffer (0.01 M Tris-HCl and 0.1 M NaCl, pH 7.8), (Fisher Scientific, USA). Lysate dilutions were added to 700 μL of cells (1×10⁸ CFU/mL), incubated for 2 hr at experimental room temperature prior to adding 5 ml of top LB agar (LB broth+0.7% agar, Bacto Agar from Difco Laboratories, Sparks, Md.) and plates were incubated overnight at 37° C. Plate lysates were then prepared by adding 10 mL of ice cold TN buffer to the surface of the plate, incubating overnight at 4° C., then transferring the solution and top agar to a conical tube, mixed and centrifuged at 8000 RPM (Hettich, Germany) at 4° C. for 20 min. The supernatant was poured into a fresh ice-cold (0° C.) conical tube and 2 μL of chloroform was added. Lysates were then precipitated by centrifuging at 8000 RPM at 4° C. for 10 min. The supernatant was removed and transferred into a new sterile tube. Then 1 μL DNase (Sina Colon, IRAN) was added to the lysate to remove any remaining free DNA in the lysate. The lysates were then passed through a 0.45 μm filter (BD Discardit, India) and kept at 4° C. for further experiments.

For phage purification polyethylene glycol (PEG)-8000 (Fisher Scientific, USA) was added to a final concentration of 10% (w/v). The bacteriophage particles were then recovered by centrifuging at 8000 RPM (Hettich, Germany) at 4° C. for 10 min. The supernatant was discarded and 1 ml TN buffer was added to the pellet and kept at 4° C. for overnight. To separate PEG and cell debris from the phage nanoparticles, an equal volume of chloroform was added. The mixture was vortexed gently for 30 seconds and spun at 4,300 RPM (Hettich, Germany) at 4° C. for 15 min. The aqueous phase, which contained the bacteriophage particles, was then removed. The solution was filtered through a sterile 0.45 μm filter (BD Discardit, India). To remove endotoxin (LPS), 1% Triton x-114 was added and the solution was shaken at 4° C. for 30 min (Innova 4080 Incubator shaker). Then the solution was incubated at 37° C. for 10 min and spun 14,000 RPM (Hettich, Germany) at 25° C. for 10 min. To completely eliminate endotoxin the phage purification procedure repeated three times. The phage solutions were titered at each step of purification by standard viability assays on fresh Sup⁺ BB4 (supE, supF) E. coli cells. Samples were stored at 4° C.

Animals and Cell Lines

Four to six week-old female BALB/c mice were purchased from Pasteur Institute (Tehran-Iran). All procedures involving animal work were approved by the Institutional Ethical Committee and Research Advisory Committee of Mashhad University of Medical Sciences in accordance with animal welfare guidelines. TUBO, a cloned cell line that overexpressed the rHER2/neu protein, was kindly provided by Dr. Pier-Luigi Lollini (Department of Clinical and Biological Sciences, University of Turin, Orbassano, Italy) and was cultured in Dulbecco's Modified Eagle's Medium (DMEM) and supplemented with 20% fetal bovine serum (FBS). CT26, a murine colon carcinoma cell line was purchased from Pasture Institute (Tehran-Iran) and cultured in RPMI-1640 medium supplemented with 10% FBS. CT26 cells were rHER2/neu negative and used as negative controls.

Immunization of BALB/c Mice

BALB/c mice were divided into three groups (ten mice per group). GP2 displaying phages (10⁸ PFU in 100 μL) per mouse was injected subcutaneously (SC) three times at two-week intervals. λ F7 (10⁸ PFU in 100 μL) and 100 μL TN buffer (per mouse) were used as controls. Two weeks after the last booster, three mice per group were sacrificed. Then the sera and splenocytes were aseptically removed and the cellular immune responses were evaluated.

ELISA

Enzyme linked immunosorbent assay (ELISA) was performed to detect the absolute quantity of cytokines. Blood samples were collected 14 d after the third immunization from the mice and were allowed to clot for 2 h at room temperature before centrifugation for 20 min at 1000×g. Sera were then isolated from the clot and stored at −20° C. or −80° C. until used. The concentrations of IFN-γ and IL-4 in the sera were determined by commercial ELISA kits according to the manufacturer's instructions (eBioscience, San Diego, Calif., USA). All assays were performed in triplicate.

In Vitro CTL Activity Assay

Two weeks after the final vaccination, mice were sacrificed and splenocytes were harvested by ammonium chloride lysis buffer (NH₄Cl 0.16 M and Tris 0.17 M). Viable splenocytes were counted using trypan blue (0.4%, w/v) and re-stimulation was performed with 10⁸ GP2-display phage in 100 μL volume. TUBO cells (target cells) were incubated with 12.5 μM calceine AM (Calcein-AM, Invitrogen, USA) at 37° C. for 1 h in dark. Triton X-100 (2%) and culture medium were added to the maximum and minimum release wells respectively. Fluorescence intensity was measured at 485 nm (excitation) and of 538 nm (emission) using a fluorescent plate reader (FLX 800, BioTek Instruments Inc. USA). The percentage of specific lysis was calculated by the following formula: (release by CTLs-minimum release by targets)/(maximum release by targets-minimum release by targets). To show the specificity of cytotoxic activity, non-expressing rHER2/neu CT26 cells were used as negative controls.

Real-Time Quantitative Reverse Transcription PCR

Real-time Reverse Transcription-PCR (RT-PCR) assay was used to evaluate INF-γ and IL-4 cytokines mRNA expression in splenocytes isolated from spleen immunized mice. Total RNA was extracted from homogenized spleen tissue using high pure RNA tissue kit (Roche, Germany) as instructed by the manufacturer. The extracted RNA was quantified using a Nano Drop spectrophotometer (ND-1000) and samples were stored at −80° C. until use. Total RNA (100 ng) was used in real time RT-PCR using one-step SYBR Green real time RT-PCR kit according to the manufacturer's instructions (Invitrogen, California, USA). The Applied Biosystems StepOne Real-time PCR System (Life Technologies Corporation, Carlsbad, Calif.) was used for one-step real time RT-PCR amplification and SYBR Green fluorescence detection. Three pairs of primers were separately used: two pairs to amplify INF-γ (F: GCTCTGAGA-CAATGAACGCT; R: AAAGAGATAATCTGGCTCTGC), and IL-4 genes (F: TCGGCATTTTGAACGAGGTC; R: GAAAAGCCCGAAAGAGTCTC and the other pair for the endogenous control gene β-actin (F: TGACCGGCTTGTAT-GCTATC and R: CAGTGTGAGCCAGGATATAG). A negative control was included in each run to assess specificity of primers and possible contamination. The possibility of nonspecific amplification or primer-dimmer formation was checked using melt curve analysis. The comparative CT (threshold cycle) method was used to evaluate fold changes of mRNA levels in immunized group relative to the control group. The fluorescence CT was calculated using Step One System software. The mRNA levels were normalized to the endogenous reference gene β-actin (ΔCT) and then relative to a control group (ΔΔCT), subsequently fold changes were expressed as "$\log_2 [2(-\Delta\Delta CT)]$". The average was calculated from three runs per sample.

In Vivo Prophylactic Studies

Fourteen days after the last vaccination, 5×10⁸ TUBO cells in 50 μL PBS buffer were injected SC in the right flank of immunized mice (seven mice per group). Mice were monitored every day. Three orthogonal diameters of the developing tumor (a, b, c) were measured with a digital caliper. The tumor volumes were calculated according to the formulation [(height×width×length)×0.5]. The equation of the line obtained by exponential regression of the tumor growth curve was used for TTE (time to reach the end point) and based on the difference between the median TTE of treatment group (T) and the median TTE of the control group (C) were used to calculate the percent TGD (the percent of tumor growth delay) (TGD %=[(T−C)/C]×100]) for each mouse. For ethical considerations, mice were sacrificed if the following conditions observed; the tumor volume was greater than 1000 mm³, the body weight loss was over 15% of initial weight or the mice became sick and unable to feed.

In Vivo Therapeutic Studies

To evaluate the anti-tumor efficacy of GP2 displaying phages and control λ F7, 5×10⁸ TUBO cells in 50 μL PBS buffer were injected in the right flank of 4-6 week old female BALB/c mice, two weeks after tumor inoculation, 10⁸ PFU of GP2 displaying and λ F7 (100 μL/mouse) were injected subcutaneously (SC) three times at 2-weeks intervals. The TN buffer and λ F7 were used as control groups. Mice were monitored every day and the tumor volume was calculated as mentioned above.

Statistical Analysis

Descriptive statistics, One-way ANOVA and Tukey test, Independent T-test and Log-rank test for survival analysis were used to assess the significance of the difference among various formulations (Graph Pad Prism Software, version 6, San Diego, Calif.). The P value<0.05 (P<0.05) was considered to be statistically significant.

Results

High Levels of INF-γ in gpD::GP2 Group Demonstrated by ELISA

To determine the induction of anti-tumor T-cell response, sera was harvested from immunized mice 14 days after the last injection. The ELISA assay showed that gpD::GP2 group produced significant secretion of IFN-γ in mice in comparison to other groups (p<0.0001). None of the gpD::GP2 and λ F7 induced the sizable IL-4 response in mice (FIG. 1)

Antigen-Specific Cytotoxicity of gpD::GP2

Figure 2:
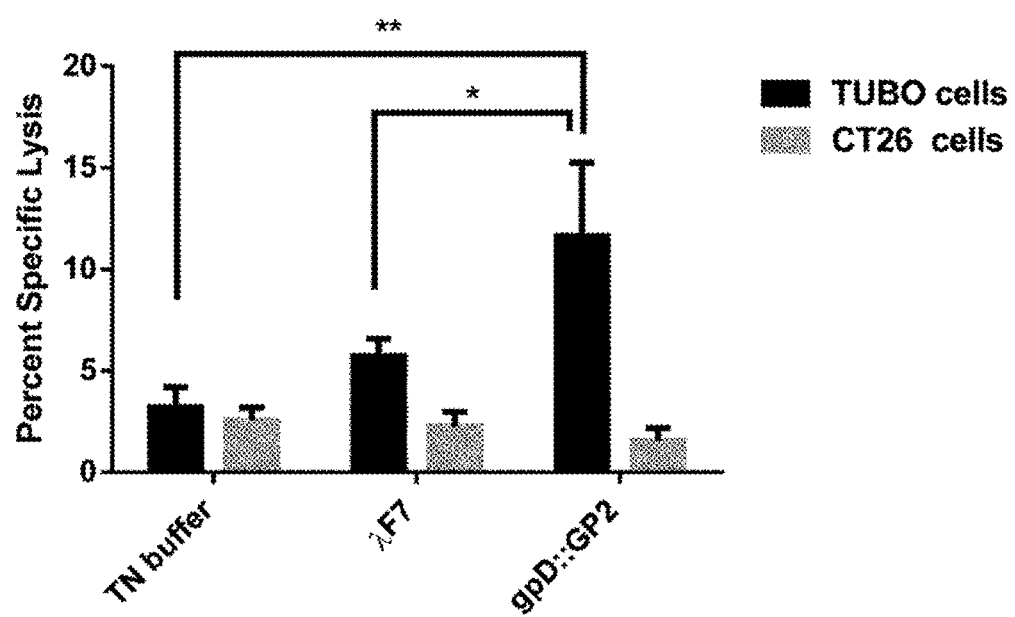
FIG. 2 shows in vitro antigen-specific CTL response of splenocytes isolated from vaccinated mice. The CTL response was assessed by calcein AM-loaded rHER2/neu-expressing TUBO cells and rHER2/neu negative CT26 cells. Data are shown as mean±SEM. (n=3). *P<0.5 and **P<0.01; denotes significant difference from controls.

Cytotoxicity assays provide an in vitro evaluation of the lytic activity of T cells against tumors. The gpD::GP2 phage was significantly effective in generating CTL response and reacted with the TUBO cell line expressing rHER2/neu in comparison with the TN buffer (p<0.01) and λ F7 groups (P<0.05). This response was antigen specific because the CTL response was not observed against CT26 tumor cells (rHER2/neu-expressing negative cells) (FIG. 2).

High Expression of IFN-γ in gpD::GP2 Group

Based on the expression of IFN-γ and IL-4, the gpD::GP2 group showed the highest levels of CTL response in the immunized mice compared to the other groups. This was supported by real time RT-PCR analysis indicating that the gpD::GP2 group modulated mRNA expression of both IFN-γ and IL-4 cytokines in favor of CTL immune response effectively.

Figure 3A:
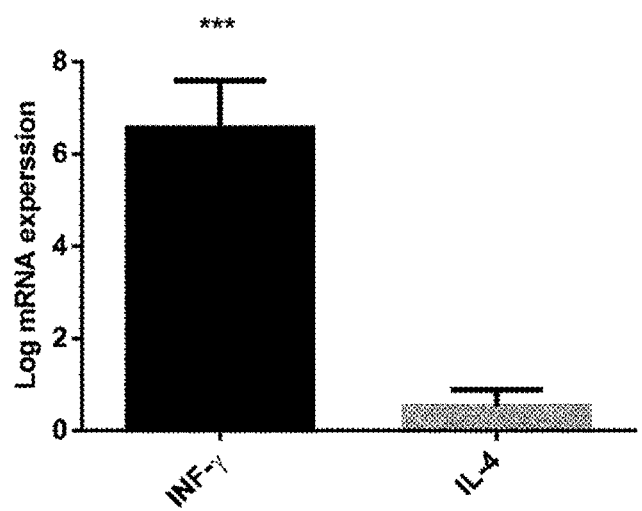
FIGS. 3A-3B show high expressions of IFN-γ and IL-4 in splenocytes isolated from BALB/c mice vaccinated with gpD::GP2 two weeks after the final vaccination with $10^8$ PFU gpD::GP2 and $10^8$ PFU λ F7.
Figure 3B:
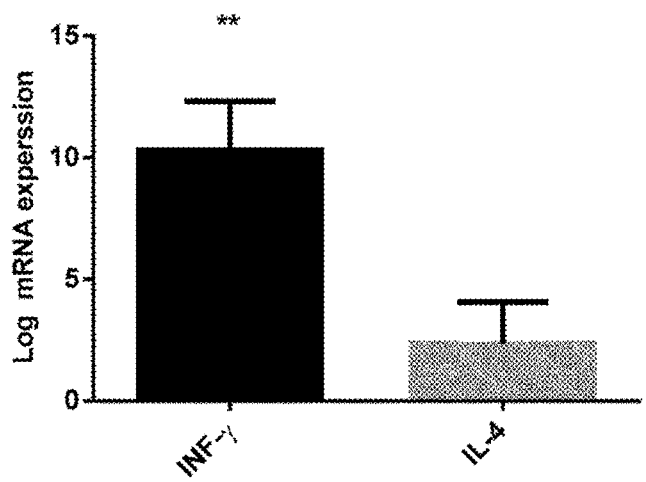

The results demonstrated that IFN-γ was increased by 6.56±1 (P<0.001) in mice immunized with gpD::GP2 splenocytes compared to the TN buffer group 14 days after the last immunization, whereas log of fold changes in IL-4 expression was found to be decreased by 0.53±0.3 (FIG. 3A). In the gpD::GP2 group IFN-γ and IL-4 expression compared with the λ F7 group. It was demonstrated that in gpD::GP2 group IFN-γ was increased by 10.31±2 (p<0.01) and IL-4 decreased by 2.34±1.7 compared to the control (FIG. 3B).

Prophylactic Assays

Figure 4A:
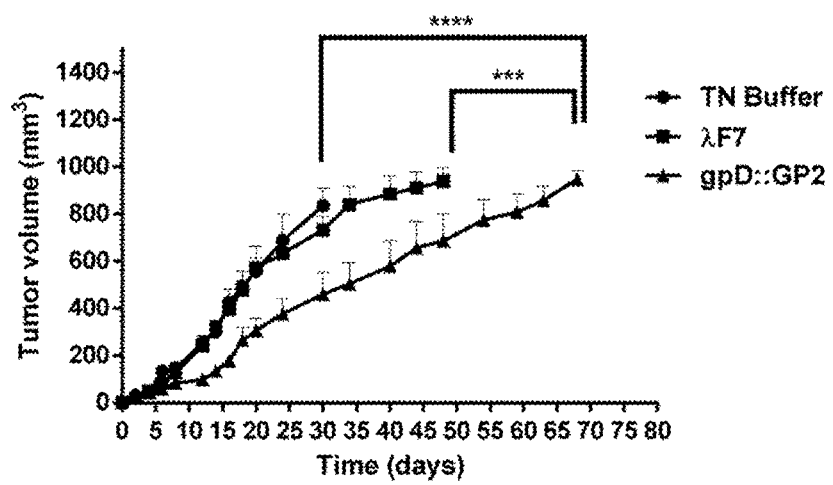
FIGS. 4A-4B show prophylactic effects of vaccination with gpD::GP2 in BALB/c mice against a TUBO tumor model. Two weeks after the last booster five mice in each group were challenged subcutaneously with $5×10^5$ TUBO cells. Mice were observed for tumor growth as shown in FIG. 4A, and survival as shown in FIG. 4B. Tumor size was calculated for two times each week, based on the three dimensions. The survival of mice was followed for 70 days. The data indicate mean±SEM (n=7). *P<0.001 and **P<0.0001; denotes significant difference from the control groups.

Tumor growth curve analysis indicated that the gpD::GP2 group was the most effective group in terms of reducing the growth rate of the tumor (p<0.0001) in comparison with TN buffer and the λF7 groups (P<0.001) (FIG. 4A). The prophylactic effects observed in mice model groups are summarized in Table 1 indicating median survival time (MST), time to reach end point (TTE) and tumor growth delay (% TGD) for each mice group.

TABLE 1

Prophylactic efficacy of different vaccine
groups in TUBO tumor model of mice (n = 7)

| Group    | MST[a] (day) | TTE[b] (day ± SD) | TGD[c] (%) |
|----------|--------------|-------------------|------------|
| TN buffer | 35          | 32 ± 5.4          | —          |
| λ F7     | 42           | 48 ± 13.7         | 51         |
| gpD::GP2 | 68           | 61 ± 13.0         | 89****     |

[a]Median survival time.
[b]Time to reach end point.
[c]Tumor growth delay.
****Denotes significant difference from all other formulations.

Figure 4B:
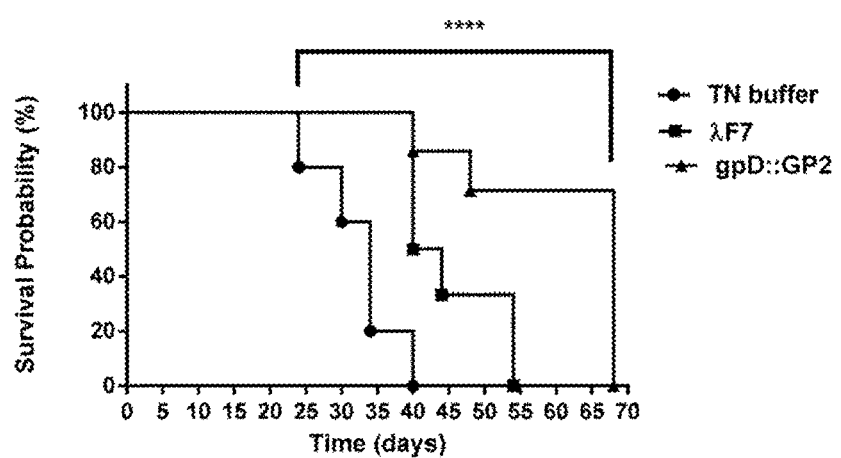

Survival analysis (up to 60 days) revealed that the gpD::GP2 group had significantly prolonged MST, TTE and % TGD versus the TN buffer (P<0.0001) (FIG. 4B).

Therapeutic Assays

Figure 5A:
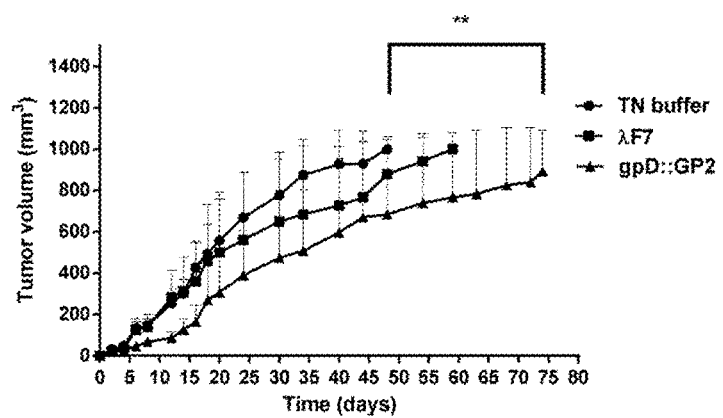
FIGS. 5A-5B show therapeutic effects of gpD::GP2 phage nanoparticles against the TUBO tumor model of BALB/c mice. Two weeks after injection of $5×10^5$ TUBO cells (five mice for each group), the mice were administrated with the gpD::GP2 phage nanoparticles for three times at two weeks interval. After the first injection the mice were challenged and tumor size was calculated based on three dimensions.
Figure 5B:
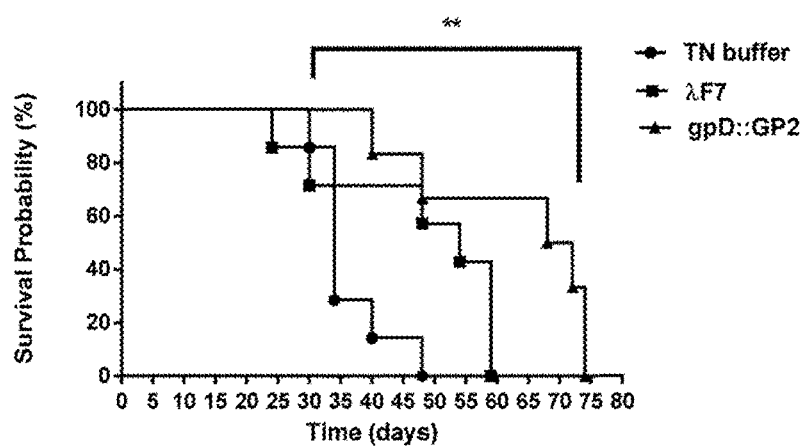

Following the observation of a considerable T-cell response in immunized mice, the anti-tumor activity of the sample in TUBO tumor model was evaluated. Among different groups, the gpD::GP2 group was superior in inhibition of tumor growth rate compared to the TN buffer (P<0.01) and λF7 groups (P<0.05) (FIG. 5A). The therapeutic efficacy of the groups is summarized in Table 2 indicating median survival time (MST), time to reach end point (TTE) and tumor growth delay (TGD %) for each mice group. The survival analysis results represented in a Kaplan-Meier plot were used to analyze significant differences in therapeutic efficacy between the control groups. Survival data showed that mice treated with gpD::GP2 had the longest MST, TTE and % TGD in comparison to the TN buffer group (P<0.01).

TABLE 2

Therapeutic efficacy data against the
TUBO tumor model of mice (n = 7)

| Group    | MST[a] (day) | TTE[b] (day ± SD) | TGD[c] (%) |
|----------|--------------|-------------------|------------|
| TN buffer | 34          | 38 ± 8.3          | —          |
| λ F7     | 54           | 46 ± 15.9         | 11         |
| gpD::GP2 | 70           | 58 ± 17.1         | 53**       |

[a]Median survival time.
[b]Time to reach end point.
[c]Tumor growth delay.

** Denotes significant difference from all other formulations.

This study was aimed to investigate the immunogenicity and anti-tumor activity of the chimeric λ phage nanoparticles displaying immunogenic GP2 peptide derived from HER-2/neu. The GP2 peptide, a TAA has a broad applicability as a cancer immunogen with low toxicity that could decrease the risk of recurrence in women with HER2/neu over-expressing breast cancer. Brossart et al. (2000), reported that injection of GP2 and GP2-pulsed dendritic cells against metastatic breast cancer and advanced ovarian cancer patients induced CTL immune response. Furthermore, GP2 based vaccines are effective in stimulating peptide-specific immunity, especially in CD8+ T cell stimulation with anti-tumor activity in human leukocyte antigen (HLA)-A2+ breast cancer patients. Recent studies revealed that patients vaccinated with GP2+GM-CSF showed a 37% reduction in cancer recurrence compared to unvaccinated patients, and those who received GM-CSF alone showed 57% reduction in risk of cancer recurrence. These patients experienced grade 1 local and systemic toxicity due to the GM-CSF with symptoms including: headache, fatigue, erythema, pruritus, bone pain, myalgia and flu-like symptoms. GM-CSF can induce antitumor immune response; however, it promotes cancer cell proliferation and migration in the different types of solid tumors such as skin carcinoma, gliomas, lung cancer and cancer cell line.

Peptides alone have a poor immunogenic profile as well as short life-spans; both intracellular and in serum. Soluble antigens cannot enter the appropriate intracellular compartment to undergo processing and presentation on class I MHC molecules. Suitable delivery systems based on immune-stimulating complexes that have a long circulation time and tendency to be taken up more efficiently by APCs to induce CTL response can therefore provide considerable improvement vaccination. Recently, bacteriophages have been sought after as an attractive alternative in novel vaccine research, particularly as delivery platforms for peptide and protein-based vaccines against infectious diseases and cancer. The efficacy of bacteriophage-driven APC delivery and cross-presentation has been proven in comparison to free antigens. This increase in efficacy has been shown by greater cellular uptake, higher immunogenicity levels in addition to the lower costs seen in bacteriophage production. Bacteriophages are endogenous adjuvants, aiding in the direction of the immune response.

In different research settings, M13 and f1 (filamentous phages) have been most widely used for bacteriophage deliveries. However, phage λ is not only capable of displaying large proteins via gpD fusions, but it can also tolerate a density where approximately 90% of the incorporated D protein is a fusion. The λ library displayed a 100-fold higher display for all fragments compared to filamentous phage when tested using an antibody binding assay. Overall, the λ system was able to display proteins of different sizes, with the number of fusions displayed on each phage particle being 2-3 orders of magnitude greater than that of M13. Functional proteins such as λ-lactamase, luciferase (a 61 kDa protein), or even λ-galactosidase (a 465 kDa protein), have all been displayed on λ with no poor effects on viability and morphology. In recent years phage therapeutic practices also include the use of a T7 and λ for phage display to identify antigens eliciting a B cell response in cancer.

One study has shown that a hybrid M13 phage displaying epitope LKVIRK in the N-terminal region of the major coat protein (pVIII) could induce high levels of IFN-γ in the CD4+ splenocytes during one week post-inoculation in C57BL/6 mice. Filamentous phage particles containing expression cassette of Herpes Simplex Virus 1 (HSV-1) glycoprotein D could induce humoral and cellular immune responses in BALB/c mice. Clark and March (2006) showed that recombinant λ phage particles containing expression cassette of hepatitis B surface antigen (HBsAg) could induce specific antibodies in mice and rabbits. Murine pneumotropic virus (MPtV) or murine polyomavirus (MPyV) VLPs carrying an ECD-TM (extracellular plus transmembrane domain) fragment of rHER-2/neu have proven efficacy as prophylactic and therapeutic tumor vaccines against rat HER-2-positive TUBO tumors. Thomas et al. (2012), reported that hybrid DNA and peptide inoculant λ gfp10-GFP-TAT can stimulate the most specific and greatest amplitude of an IFN-γ production in female CD1 mice.

In this study, the immunogenicity and antitumor potential of the bacteriophage nanoparticles displaying the GP2 peptide derived from HER2/neu were investigated using in vivo and in vitro assays. BALB/c mice were immunized subcutaneously three times with 10^8 PFU of endotoxin-free gpD::GP2 phage nanoparticles and phage λF7 and TN buffer were selected as controls. Our data demonstrated that λ phage activity as an endogenous adjuvant. This was observed by significant IFN-γ splenocyte proliferation in the absence of an adjuvant in our inoculations. The adjuvant activity is likely linked to the λ capsid, or from bacterial pathogen-associated molecular patterns (PAMPs). Fourteen days following the last booster injection, splenocytes and sera were extracted from spleens and blood. The ELISA and cytotoxicity assays showed mice immunized with gpD::GP2 nanoparticles could induce a significantly higher INF-γ and CTL response compared control groups indicating the crucial role of repetitive display of GP2 peptide on the surface of λ nanoparticles in its immunogenicity. The CTL response was found to be associated with higher and lower amounts of IFN-γ and IL-4, respectively, in both protein and mRNA expression studies. The CTL responses elicited by vaccination of mice with the gpD::GP2 nanoparticles showed a delay in tumor growth and superior anti-tumor effects in vivo. It was indicated by a higher survival (89% vs. 51%) of mice against HER-2-over expressing TUBO cell line challenge. Also the therapeutic assay showed that gpD::GP2 nanoparticles could induce complete regression of the established tumors (53% vs. 21%). Also shown herein is that the designing of a linker (GG or GS) helps correct cross presentation of polytopes to the immune system. Yeast-derived Ty-VLPs carrying two different CTL epitopes linked by a glycine-glycine (GG) or glycine-serine (GS) spacer successfully evoked T cell responses against both epitopes. Interestingly, only the gpD::GP2 chimer in which the GP2 peptide was directly linked to gpD by an in-frame short linker contains GG and GS (T-S-G-S-G-S-G-S-G-S-G-S-G-S-G) flexible space was successfully processed and cross-presented and induced effective anti-tumor CTL responses. The data supports the previous reports that glycine and serine flanking residues enhance cross-presentation of Yeast-derived Ty-VLPs carried CTL epitopes. Finally, the in vivo anti-tumor efficacy of the phage delivery system was mediated by the induction of tumor protection in BALB/c mice vaccinated with gpD::GP2 nanoparticles. Note that bacteriophages are considerably safe in mammalian systems and their efficacy has been shown in humans, despite the host induced the production of anti-bacteriophage Abs.

Thus, it has been demonstrated herein that the delivery of GP2 peptide displayed on a nonpathogenic λ bacteriophage has significantly enhanced the anti-tumor immune function compared to the control groups. This attests to the potential of the gpD::GP2 phage nanoparticles for vaccine delivery as both protective and inhibitors of tumor against Her2/neu overexpressing breast cancer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

1. Disis, M. L., et al., *Pre-existent immunity to the HER-2/neu oncogenic protein in patients with HER-2/neu over-expressing breast and ovarian cancer*. Breast cancer research and treatment, 2000. 62(3): p. 245-252.
2. Spurrell, E. L. and M. Lockley, *Adaptive immunity in cancer immunology and therapeutics*. Ecancermedicalscience, 2014. 8.
3. Parmiani, G., et al., *Universal and stemness-related tumor antigens: potential use in cancer immunotherapy*. Clinical Cancer Research, 2007. 13(19): p. 5675-5679.
4. Purcell, A. W., J. McCluskey, and J. Rossjohn, *More than one reason to rethink the use of peptides in vaccine design*. Nature reviews Drug discovery, 2007. 6(5): p. 404-414.
5. Baxevanis, C. N., et al., *Immunogenic HER-2/neu peptides as tumor vaccines*. Cancer Immunology, Immunotherapy, 2006. 55(1): p. 85-95.
6. Mittendorf, E. A., et al., *Evaluation of the HER2/neu-derived peptide GP2 for use in a peptide-based breast cancer vaccine trial*. Cancer, 2006. 106(11): p. 2309-2317.
7. Sue, R., *New peptide vaccine for HER2-expressing breast tumors*. Journal of the National Cancer Institute, 2015. 107(2): p. djv022.
8. Mittendorf, E. A., et al., *Evaluation of the CD107 cytotoxicity assay for the detection of cytolytic CD8+ cells recognizing HER2/neu vaccine peptides*. Breast cancer research and treatment, 2005. 92(1): p. 85-93.
9. Brossart, P., et al., *Induction of cytotoxic T-lymphocyte responses in vivo after vaccinations with peptide pulsed dendritic cells*. Blood, 2000. 96(9): p. 3102-3108.
10. Barati, N., et al., *Nanoliposomes carrying HER2/neu-derived peptide AE36 with CpG-ODN exhibit therapeutic and prophylactic activities in a mice TUBO model of breast cancer*. Immunology Letters, 2017.
11. Souza, A., et al., *Recombinant viruses as vaccines against viral diseases*. Brazilian Journal of Medical and Biological Research, 2005. 38(4): p. 509-522.
12. De la Cruz, V., A. Lal, and T. F. McCutchan, *Immunogenicity and epitope mapping of foreign sequences via genetically engineered filamentous phage*. Journal of Biological Chemistry, 1988. 263(9): p. 4318-4322.
13. Ulivieri, C., et al., *Antigenic properties of HCMV peptides displayed by filamentous bacteriophages vs. synthetic peptides*. Immunology letters, 2008. 119(1): p. 62-70.
14. Gao, J., et al., *Phage display and its application in vaccine design*. Annals of microbiology, 2010. 60(1): p. 13-19.
15. Hayes, S., L. N. Gamage, and C. Hayes, *Dual expression system for assembling phage lambda display particle (LDP) vaccine to porcine Circovirus 2 (PCV2)*. Vaccine, 2010. 28(41): p. 6789-6799.
16. Sartorius, R., et al., *The use of filamentous bacteriophage fd to deliver MAGE-A10 or MAGE-A3 HLA-A2-restricted peptides and to induce strong antitumor CTL responses*. The Journal of Immunology, 2008. 180(6): p. 3719-3728.
17. De Berardinis, P., et al., *Phage display of peptide epitopes from HIV-1 elicits strong cytolytic responses*. Nature biotechnology, 2000. 18(8): p. 873-876.
18. Hashemi, H., et al., *Immunization with M2e-displaying T7 bacteriophage nanoparticles protects against influenza A virus challenge*. PloS one, 2012. 7(9): p. e45765.
19. Beghetto, E. and N. Gargano, *Lambda-display: a powerful tool for antigen discovery*. Molecules, 2011. 16(4): p. 3089-3105.
20. Suzuki, D. T. and A. J. Griffiths, *An introduction to genetic analysis*. 1976: WH Freeman and Company.
21. Malik, P., et al., *Role of capsid structure and membrane protein processing in determining the size and copy*

21. number of peptides displayed on the major coat protein of filamentous bacteriophage. Journal of molecular biology, 1996. 260(1): p. 9-21.
22. Yang, F., et al., *Novel fold and capsid-binding properties of the λ-phage display platform protein gpD*. Nature Structural & Molecular Biology, 2000. 7(3): p. 230-237.
23. Mikawa, Y. G., I. N. Maruyama, and S. Brenner, *Surface display of proteins on bacteriophage λ heads*. Journal of molecular biology, 1996. 262(1): p. 21-30.
24. Sternberg, N. and R. H. Hoess, *Display of peptides and proteins on the surface of bacteriophage lambda*. Proceedings of the National Academy of Sciences, 1995. 92(5): p. 1609-1613.
25. Minenkova, O., et al., *Identification of tumor-associated antigens by screening phage-displayed human cDNA libraries with sera from tumor patients*. International journal of cancer, 2003. 106(4): p. 534-544.
26. Sokolenko, S., et al., *Graphical analysis of flow cytometer data for characterizing controlled fluorescent protein display on λ phage*. Cytometry Part A, 2012. 81(12): p. 1031-1039.
27. Lichtenfels, R., et al., *CARE-LASS (calcein-release-assay), an improved fluorescence-based test system to measure cytotoxic T lymphocyte activity*. Journal of immunological methods, 1994. 172(2): p. 227-239.
28. Kopf, M., et al., *IL-4-deficient Balb/c mice resist infection with Leishmania major*. Journal of Experimental Medicine, 1996. 184(3): p. 1127-1136.
29. Spergel, J. M., et al., *Epicutaneous sensitization with protein antigen induces localized allergic dermatitis and hyperresponsiveness to methacholine after single exposure to aerosolized antigen in mice*. Journal of Clinical Investigation, 1998. 101(8): p. 1614.
30. Huang, Z., M. R. Jaafari, and F. C. Szoka, *Disterolphospholipids: nonexchangeable lipids and their application to liposomal drug delivery*. Angewandte Chemie International Edition, 2009. 48(23): p. 4146-4149.
31. Brunner, K., et al., *Quantitative assay of the lytic action of immune lymphoid cells of 51Cr-labelled allogeneic target cells in vitro; inhibition by isoantibody and by drugs*. Immunology, 1968. 14(2): p. 181.
32. Schneble, E. J., et al. *Primary analysis of the prospective, randomized, phase II trial of GP2+GM-CSF vaccine versus GM-CSF alone administered in the adjuvant setting to high-risk breast cancer patients*. in ASCO Annual Meeting Proceedings. 2014.
33. Carmichael, M. G., et al., *Results of the first phase 1 clinical trial of the HER-2/neu peptide (GP2) vaccine in disease-free breast cancer patients*. Cancer, 2010. 116(2): p. 292-301.
34. Gutschalk, C. M., et al., *GM-CSF enhances tumor invasion by elevated MMP-2, -9, and -26 expression*. Cancer medicine, 2013. 2(2): p. 117-129.
35. Bona, C. A., S. Casares, and T.-D. Brumeanu, *Towards development of T-cell vaccines*. Immunology today, 1998. 19(3): p. 126-133.
36. Bot, A., et al., *Kinetics of generation and persistence on membrane class II molecules of a viral peptide expressed on foreign and self proteins*. The Journal of Immunology, 1996. 157(8): p. 3436-3442.
37. Chikh, G. G., et al., *Efficient delivery of Antennapedia homeodomain fused to CTL epitope with liposomes into dendritic cells results in the activation of CD8+ T cells*. The Journal of Immunology, 2001. 167(11): p. 6462-6470.
38. Nilsson, F., et al., *The use of phage display for the development of tumour targeting agents*. Advanced drug delivery reviews, 2000. 43(2): p. 165-196.
39. De Temmerman, M.-L., et al., *Particulate vaccines: on the quest for optimal delivery and immune response*. Drug discovery today, 2011. 16(13): p. 569-582.
40. Prisco, A. and P. De Berardinis, *Filamentous bacteriophage fd as an antigen delivery system in vaccination*. International journal of molecular sciences, 2012. 13(4): p. 5179-5194.
41. Zucconi, A., et al., *Selection of ligands by panning of domain libraries displayed on phage lambda reveals new potential partners of synaptojanin 1*. Journal of molecular biology, 2001. 307(5): p. 1329-1339.
42. Gupta, A., et al., *High-density functional display of proteins on bacteriophage lambda*. Journal of molecular biology, 2003. 334(2): p. 241-254.
43. Eguchi, A., et al., *Protein transduction domain of HIV-1 Tat protein promotes efficient delivery of DNA into mammalian cells*. Journal of Biological Chemistry, 2001. 276(28): p. 26204-26210.
44. Kalnioa, Z., et al., *Evaluation of T7 and lambda phage display systems for survey of autoantibody profiles in cancer patients*. Journal of immunological methods, 2008. 334(1): p. 37-50.
45. Yang, Q., et al., *Prophylactic vaccination with phage-displayed epitope of C. albicans elicits protective immune responses against systemic candidiasis in C57BL/6 mice*. Vaccine, 2005. 23(31): p. 4088-4096.
46. Hashemi, H., et al., *Evaluation of humoral and cellular immune responses against HSV-1 using genetic immunization by filamentous phage particles: a comparative approach to conventional DNA vaccine*. Journal of virological methods, 2010. 163(2): p. 440-444.
47. Clark, J. R. and J. B. March, *Bacterial viruses as human vaccines?* Expert review of vaccines, 2004. 3(4): p. 463-476.
48. Andreasson, K., et al., *Murine pneumotropic virus chimeric Her2/neu virus-like particles as prophylactic and therapeutic vaccines against Her2/neu expressing tumors*. International journal of cancer, 2009. 124(1): p. 150-156.
49. Thomas, B. S., et al., *Peptide vaccination is superior to genetic vaccination using a recombineered bacteriophage λ subunit vaccine*. Vaccine, 2012. 30(6): p. 998-1008.
50. Layton, G., et al., *Induction of single and dual cytotoxic T-lymphocyte responses to viral proteins in mice using recombinant hybrid Ty-virus-like particles*. Immunology, 1996. 87(2): p. 171-178.
51. Clark, J. R. and J. B. March, *Bacteriophages and biotechnology: vaccines, gene therapy and antibacterials*. Trends in biotechnology, 2006. 24(5): p. 212-218.

SEQUENCES

```
SEQ ID NO: 1 gpD
ATGACGAGCAAAGAAACCTTTACCCATTACCAGCCGCAGGGCAACAGTGA
CCCGGCTCATACCGCAACCGCGCCCGGCGGATTGAGTGCGAAAGCGCCTG
CAATGACCCCGCTGATGCTGGACACCTCCAGCCGTAAGCTGGTTGCGTGG
GATGGCACCACCGACGGTGCTGCCGTTGGCATTCTTGCGGTTGCTGCTGA
CCAGACCAGCACCACGCTGACGTTCTACAAGTCCGGCACGTTCCGTTATG
AGGATGTGCTCTGGCCGGAGGCTGCCAGCGACGAGACGAAAAAACGGACC
GCGTTTGCCGGAACGGCAATCAGCATCGTT

SEQ ID NO: 2 gpD
MTSKETFTHYQPQGNSDPAHTATAPGGLSAKAPAMTPLMLDTSSRKLVAW
DGTTDGAAVGILAVAADQTSTTLTFYKSGTFRYEDVLWPEAASDETKKRT
AFAGTAISIV
```

SEQUENCES

SEQ ID NO: 3 linker
ACTAGCGGTTCCGGTTCTGGTTCCGGTTCTGGTTCCGGTTCTGGC

SEQ ID NO: 4 linker
TSGSGSGSGSGSGSG

SEQ ID NO: 5 GP2 antigen
ATTATTAGCGCGGTGGTGGGCATTCTGTAG

SEQ ID NO: 6 GP2 antigen
IISAVVGIL

SEQ ID NO: 7 E75 antigen
AAAATTTTTGGCAGCCTGGCGTTTCTGTAG

SEQ ID NO: 8 E75 antigen
KIFGSLAFL

SEQ ID NO: 9 AE37 antigen
CTGCGCATGAAAGGCGTGGGCAGCCCCGTATGTGAGCCGCCTGCTGGGCATTTGCCTGTAG SEQ ID NO: 10 AE37 antigen
LRMKGVGSPYVSRLLGICL SEQ ID NO: 11 gpD-linker-GP2
ATGACGAGCAAAGAAACCTTTACCCATTACCAGCCGCAGGGCAACAGTGACCCGGCTCATACCGCAACCGCGCCCGGCGGATTGAGTGCGAAAGCGCCTGCAATGACCCCGCTGATGCTGGACACCTCCAGCCGTAAGCTGGTTGCGTGGGATGGCACCACCGACGGTGCTGCCGTTGGCATTCTTGCGGTTGCTGCTGACCAGACCAGCACCACGCTGACGTTCTACAAGTCCGGCACGTTCCGTTATGAGGATGTGCTCTGGCCGGAGGCTGCCAGCGACGAGACGAAAAAACGGACCGCGTTTGCCGGAACGGCAATCAGCATCGTTACTAGCGGTTCCGGTTCTGGTTCCGGTTCTGGCGGTACCATTATTAGCGCGGTGGTGGCATTCTGTAG SEQ ID NO: 12 gpD-linker-GP2
MTSKETFTHYQPQGNSDPAHTATAPGGLSAKAPAMTPLMLDTSSRKLVAW
DGTTDGAAVGILAVAADQTSTTLTFYKSGTFRYEDVLWPEAASDETKKRT
AFAGTAISIVTSGSGSGSGS
GSGSGGTIISAVVGIL SEQ ID NO: 13 gpD-linker-E75
ATGACGAGCAAAGAAACCTTTACCCATTACCAGCCGCAGGGCAACAGTGACCCGGCTCATACCGCAACCGCGCCCGGCGGATTGAGTGCGAAAGCGCCTGCAATGACCCCGCTGATGCTGGACACCTCCAGCCGTAAGCTGGTTGCGTGGGATGGCACCACCGACGGTGCTGCCGTTGGCATTCTTGCGGTTGCTGCTGACCAGACCAGCACCACGCTGACGTTCTACAAGTCCGGCACGTTCCGTTATGAGGATGTGCTCTGGCCGGAGGCTGCCAGCGACGAGACGAAAAAACGGACCGCGTTTGCCGGAACGGCAATCAGCATCGTTACTAGCGGTTCCGGTTCTGGTTCCGGTTCTGGCGGTACCAAAATTTTTGGCAGCCTGGCGTTTCTGTAG SEQ ID NO: 14 gpD-linker-E75
MTSKETFTHYQPQGNSDPAHTATAPGGLSAKAPAMTPLMLDTSSRKLVAW
DGTTDGAAVGILAVAADQTSTTLTFYKSGTFRYEDVLWPEAASDETKKRT
AFAGTAISIVTSGSGSGSGS
GSGSGGTKIFGSLAFL SEQ ID NO: 15 gpD-linker-AE37
ATGACGAGCAAAGAAACCTTTACCCATTACCAGCCGCAGGGCAACAGTGACCCGGCTCATACCGCAACCGCGCCCGGCGGATTGAGTGCGAAAGCGCCTGCAATGACCCCGCTGATGCTGGACACCTCCAGCCGTAAGCTGGTTGCGTGGGATGGCACCACCGACGGTGCTGCCGTTGGCATTCTTGCGGTTGCTGCTGACCAGACCAGCACCACGCTGACGTTCTACAAGTCCGGCACGTTCCGTTATGAGGATGTGCTCTGGCCGGAGGCTGCCAGCGACGAGACGAAAAAACGGACCGCGTTTGCCGGAACGGCAATCAGCATCGTTACTAGCGGTTCCGGTTCTGGTTCCGGTTCTGGCGGTACCCTGCGCATGAAAGGCGTGGGCAGCCCCGTATGTGAGCCGCCTGCTGGGCATTTGCCTGTAG SEQ ID NO: 16 gpD-linker-AE37
MTSKETFTHYQPQGNSDPAHTATAPGGLSAKAPAMTPLMLDTSSRKLVAW
DGTTDGAAVGILAVAADQTSTTLTFYKSGTFRYEDVLWPEAASDETKKRT
AFAGTAISIVTSGSGSGSGSGSGGTLRMKGVGSPYVSRLLGICL

What is claimed is:

1. A fusion protein comprising bacteriophage λ gpD fused to a GP2 antigen derived from HER-2/neu and a linker linking the gpD and the GP2 antigen, wherein the linker comprises a GG repeat, a GS repeat, or a combination thereof.

2. The fusion protein of claim 1, wherein the gpD consists of or comprises an amino acid sequence at least about 90%, 95%, 97%, 98%, 99% or 100% identical to the amino acid sequence set forth in SEQ ID NO: 2.

3. The fusion protein of claim 1, wherein the GP2 antigen consists of or comprises the amino acid sequence set forth in SEQ ID NO: 6.

4. The fusion protein of claim 1, wherein the GP2 antigen is immunogenic.

5. The fusion protein of claim 1, wherein the linker consists of or comprises an amino acid sequence encoded by a nucleic acid sequence having at least 90% identity to the sequence set forth in SEQ ID NO 3.

6. The fusion protein of claim 1, wherein the linker comprises an amino acid sequence at least about 90%, 95%, 97%, 98%, 99% or 100% identical to the amino acid sequence set forth in SEQ ID NO: 4.

7. The fusion protein of claim 1, wherein the fusion protein consists of or comprises an amino acid sequence encoded by a nucleic acid sequence having at least about 90% identity to the sequence set forth in SEQ ID NO 11.

8. The fusion protein of claim 1, wherein the fusion protein consists of or comprises the amino acid sequence set forth in SEQ ID NO: 12.

9. A method for treating cancer in a subject in need thereof, comprising administering to the subject a fusion protein comprising bacteriophage λ gpD fused to a GP2 antigen derived from HER-2/neu and a linker linking the gpD and the GP2 antigen, wherein the linker comprises a GG repeat, a GS repeat, or a combination thereof.

10. The method of claim 9, wherein the cancer comprises breast cancer.

11. The method of claim 9, wherein the gpD consists of or comprises an amino acid sequence at least about 90%, 95%, 97%, 98%, 99% or 100% identical to the amino acid sequence set forth in SEQ ID NO: 2.

12. The method of claim 9, wherein the GP2 antigen consists of or comprises the amino acid sequence set forth in SEQ ID NO: 6.

13. The method of claim 9, wherein the GP2 antigen is immunogenic.

14. The method of claim 9, wherein the linker consists of or comprises an amino acid sequence encoded by a nucleic acid sequence having at least 90% identity to the sequence set forth in SEQ ID NO 3.

15. The method of claim 9, wherein the linker comprises an amino acid sequence at least about 90%, 95%, 97%, 98%, 99% or 100% identical to the amino acid sequence set forth in SEQ ID NO: 4.

16. The method of claim 9, wherein the fusion protein consists of or comprises an amino acid sequence encoded by a nucleic acid sequence having at least about 90% identity to the sequence set forth in SEQ ID NO 11.

17. The method of claim 9, wherein the fusion protein consists of or comprises the amino acid sequence set forth in SEQ ID NO: 12.

* * * * *

SEQUENCE LISTING

```
<160> NUMBER OF SEQ ID NOS: 40

<210> SEQ ID NO 1
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgacgagca agaaaccttt acccattac cagccgcagg gcaacagtga cccggctcat      60
accgcaaccg cgcccggcgg attgagtgcg aaagcgcctg caatgacccc gctgatgctg     120
gacacctcca gccgtaagct ggttgcgtgg gatggcacca ccgacggtgc tgccgttggc     180
attcttgcgg ttgctgctga ccagaccagc accacgctga cgttctacaa gtccggcacg     240
ttccgttatg aggatgtgct ctggccggag gctgccagcg acgagacgaa aaaacggacc     300
gcgtttgccg gaacggcaat cagcatcgtt                                      330

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

```
Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val
            100                 105                 110
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
actagcgggt tctggttccg gttctggttc cggttctggc                40

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Thr Ser Gly Ser Gly Ser Gly Ser Gly Ser Gly Ser Gly Ser Gly
1               5                   10                  15
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
attattagcg cggtggtggg cattctgtag                30

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Ile Ile Ser Ala Val Val Gly Ile Leu
1               5
```

<210> SEQ ID NO 7

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 aaaattttg gcagcctggc gtttctgtag                                           30

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ile Phe Gly Ser Leu Ala Phe Leu
1               5

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctgcgcatga aggcgtggg cagcccgtat gtgagccgcc tgctgggcat ttgcctgtag           60

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Arg Met Lys Gly Val Gly Ser Pro Tyr Val Ser Arg Leu Leu Gly
1               5                   10                  15

Ile Cys Leu

<210> SEQ ID NO 11
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgacgagca agaaaacctt tacccattac cagccgcagg gcaacagtga cccggctcat         60
accgcaaccg cgcccggcgg attgagtgcg aaagcgcctg caatgacccc gctgatgctg       120
gacacctcca gccgtaagct ggttgcgtgg gatggcacca ccgacggtgc tgccgttggc       180
attcttgcgg ttgctgctga ccagaccagc accacgctga cgttctacaa gtccggcacg       240
ttccgttatg aggatgtgct ctggccggag gctgccagcg acgagacgaa aaaacggacc       300
gcgtttgccg aacggcaat cagcatcgtt actagcggtt ccggtctgg ttccggttct         360 ggttccggtt ctggcggtac cattattagc gcggtggtgg gcattctgta g                411
```

<210> SEQ ID NO 12
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

Pro Ala Met Thr Pro Leu Met Leu Asp Thr Ser Arg Lys Leu Val
        35                  40                  45

Ala Trp Asp Gly Thr Thr Asp Gly Ala Ala Val Gly Ile Leu Ala Val
    50                  55                  60

Ala Ala Asp Gln Thr Ser Thr Thr Leu Thr Phe Tyr Lys Ser Gly Thr
65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Thr Ser
            100                 105                 110

Gly Ser Gly Ser Gly Ser Gly Ser Gly Ser Gly Gly Thr Ile
            115                 120                 125

Ile Ser Ala Val Val Gly Ile Leu
        130                 135

<210> SEQ ID NO 13
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgacgagca aagaaacctt tacccattac cagccgcagg gcaacagtga cccggctcat      60
accgcaaccg cgcccggcgg attgagtgcg aaagcgcctg caatgacccc gctgatgctg     120
gacacctcca gccgtaagct ggttgcgtgg gatggcacca ccgacggtgc tgccgttggc     180
attcttgcgg ttgctgctga ccagaccagc accacgctga cgttctacaa gtccggcacg     240
ttccgttatg aggatgtgct ctggccggag gctgccagcg acgagacgaa aaaacggacc     300
gcgtttgccg gaacggcaat cagcatcgtt actagcggtt ccggttctgg ttccggttct     360
ggttccggtt ctggcggtac caaaattttt ggcagcctgg cgtttctgta g             411

<210> SEQ ID NO 14
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Thr Ser Lys Glu Thr Phe Thr His Tyr Gln Pro Gln Gly Asn Ser
1               5                   10                  15

Asp Pro Ala His Thr Ala Thr Ala Pro Gly Gly Leu Ser Ala Lys Ala
            20                  25                  30

```
Pro Ala Met Thr Pro Leu Met Leu Asp Thr Ser Ser Arg Lys Leu Val
            35                  40                  45

Ala Trp Asp Gly Thr Thr Asp Gly Ala Ala Val Gly Ile Leu Ala Val
 50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Thr Ser
            100                 105                 110

Gly Ser Gly Ser Gly Ser Gly Ser Gly Ser Gly Gly Thr Lys
            115                 120                 125

Ile Phe Gly Ser Leu Ala Phe Leu
            130                 135

<210> SEQ ID NO 15
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atgacgagca agaaaacctt tacccattac cagccgcagg gcaacagtga cccggctcat      60
accgcaaccg cgcccggcgg attgagtgcg aaagcgcctg caatgacccc gctgatgctg     120
gacacctcca gccgtaagct ggttgcgtgg gatggcacca ccgacggtgc tgccgttggc     180
attcttgcgg ttgctgctga ccagaccagc accacgctga cgttctacaa gtccggcacg     240
ttccgttatg aggatgtgct ctggccggag gctgccagcg acgagacgaa aaaacggacc     300
gcgtttgccg gaacggcaat cagcatcgtt actagcggtt ccggttctgg ttccggttct     360
ggttccggtt ctggcggtac cctgcgcatg aaaggcgtgg gcagcccgta tgtgagccgc     420
ctgctgggca tttgcctgta g                                                441

<210> SEQ ID NO 16
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Thr Ser Lys Glu Thr Phe Thr His Tyr Gln Pro Gln Gly Asn Ser
 1               5                  10                  15

Asp Pro Ala His Thr Ala Thr Ala Pro Gly Gly Leu Ser Ala Lys Ala
                20                  25                  30

Pro Ala Met Thr Pro Leu Met Leu Asp Thr Ser Ser Arg Lys Leu Val
            35                  40                  45

Ala Trp Asp Gly Thr Thr Asp Gly Ala Ala Val Gly Ile Leu Ala Val
 50                  55                  60

Ala Ala Asp Gln Thr Ser Thr Thr Leu Thr Phe Tyr Lys Ser Gly Thr
 65                  70                  75                  80

Phe Arg Tyr Glu Asp Val Leu Trp Pro Glu Ala Ala Ser Asp Glu Thr
                85                  90                  95

Lys Lys Arg Thr Ala Phe Ala Gly Thr Ala Ile Ser Ile Val Thr Ser
```

```
            100                 105                 110
Gly Ser Gly Ser Gly Ser Gly Ser Gly Ser Gly Gly Thr Leu
        115                 120                 125

Arg Met Lys Gly Val Gly Ser Pro Tyr Val Ser Arg Leu Leu Gly Ile
    130                 135                 140

Cys Leu
145

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Met Thr Tyr Trp His Leu Leu Asn Ala Phe Thr Val Thr Val Pro
1               5                   10                  15

Lys Asp Leu

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Ile Leu Gly Ala Ile Leu Leu Cys Leu Gly Val Ala Leu Thr Phe
1               5                   10                  15

Ile Phe Arg Leu Arg Lys Gly
                20

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Asn Ala Phe Thr Val Thr Val
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Thr Glu Leu Leu Asn Val Cys Met Asn Ala Lys His His Lys Glu
1               5                   10                  15

Lys

<210> SEQ ID NO 21
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Gln Cys Arg Pro Trp Arg Lys Asn Ala Cys Cys Ser Thr Asn Thr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Cys Arg Pro Trp Arg Lys Asn Ala Cys Cys Ser Thr Asn Thr
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Gly Pro Trp Ile Gln Gln Val Asp Gln Ser Trp Arg Lys Glu Arg
1               5                   10                  15

Val

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Trp Ala Ala Trp Pro Phe Leu Leu Ser Leu Ala Leu Met Leu Leu
1               5                   10                  15

Trp Leu

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ala Asp Pro Thr Gly His Ser Tyr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Gly Leu Tyr Asp Gly Met Glu His Leu
1               5

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
attattagcg cggtggtggg cattctgtag                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctacagaatg cccaccaccg cgctaataat                                    30

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Tyr Lys Asp Asp Asp Asp Lys
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 30

His His His His His
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 32

Ile Ile Ser Ala Trp Gly Ile Leu
1               5

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctctgagac aatgaacgct                                          20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaagagataa tctggctctg c                                        21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcggcatttt gaacgaggtc                                          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaaaagcccg aaagagtctc                                          20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgaccggctt gtatgctatc                                          20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

```
    primer

<400> SEQUENCE: 38
cagtgtgagc caggatatag                                                  20

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Lys Val Ile Arg Lys
1               5

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
actagcggtt ccggttctgg ttccggttct ggttccggtt ctggc                      45
```